(12) United States Patent
Donde et al.

(10) Patent No.: US 9,796,696 B2
(45) Date of Patent: *Oct. 24, 2017

(54) SUBSTITUTED ARYLCYCLOPENTENES AS THERAPEUTIC AGENTS

(71) Applicant: Allergan, Inc., Irvine, CA (US)

(72) Inventors: Yariv Donde, Dana Point, CA (US); Jeremiah H. Nguyen, La Puente, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/088,964

(22) Filed: Apr. 1, 2016

(65) Prior Publication Data

US 2017/0057941 A1  Mar. 2, 2017

Related U.S. Application Data

(63) Continuation of application No. 14/273,114, filed on May 8, 2014, now Pat. No. 9,365,485, which is a continuation of application No. 12/524,305, filed as application No. PCT/US2008/051568 on Jan. 21, 2008, now Pat. No. 8,722,726.

(60) Provisional application No. 60/886,533, filed on Jan. 25, 2007.

(51) Int. Cl.
| | |
|---|---|
| *C07D 333/40* | (2006.01) |
| *C07C 59/90* | (2006.01) |
| *C07D 307/68* | (2006.01) |
| *C07D 277/56* | (2006.01) |
| *C07D 213/55* | (2006.01) |
| *C07D 409/04* | (2006.01) |
| *C07D 333/24* | (2006.01) |
| *C07D 409/10* | (2006.01) |
| *C07D 213/30* | (2006.01) |
| *C07C 65/19* | (2006.01) |
| *C07C 59/56* | (2006.01) |
| *C07C 323/52* | (2006.01) |
| *C07D 333/38* | (2006.01) |

(52) U.S. Cl.
CPC .......... *C07D 333/40* (2013.01); *C07C 59/56* (2013.01); *C07C 59/90* (2013.01); *C07C 65/19* (2013.01); *C07C 323/52* (2013.01); *C07D 213/30* (2013.01); *C07D 213/55* (2013.01); *C07D 277/56* (2013.01); *C07D 307/68* (2013.01); *C07D 333/24* (2013.01); *C07D 333/38* (2013.01); *C07D 409/04* (2013.01); *C07D 409/10* (2013.01); *C07C 2601/10* (2017.05)

(58) Field of Classification Search
CPC .................................................. C07D 333/38

USPC .......................................................... 549/71
See application file for complete search history.

(56) References Cited

U.S. PATENT DOCUMENTS

| | | | |
|---|---|---|---|
| 4,066,834 A | 1/1978 | Woessner et al. | |
| 5,902,726 A | 5/1999 | Kliewer et al. | |
| 7,091,231 B2 | 8/2006 | Donde | |
| 7,427,685 B2 | 9/2008 | Donde | |
| 8,722,726 B2 | 5/2014 | Donde et al. | |
| 2006/0205800 A1 | 9/2006 | Donde et al. | |
| 2014/0323510 A1 | 10/2014 | Donde et al. | |

FOREIGN PATENT DOCUMENTS

| | | |
|---|---|---|
| WO | WO9517393 | 6/1995 |
| WO | 95-19964 | 7/1995 |
| WO | WO9855468 | 12/1998 |
| WO | WO9926629 | 6/1999 |
| WO | WO0016760 | 3/2000 |
| WO | 2005-061449 | 7/2005 |
| WO | 2006-063179 | 6/2006 |

OTHER PUBLICATIONS

Anderson et al, The Practice of Medicinal Chemistry, 1996, 32 Pages, 3rd Edition.
Andrew G. Myers, Pseudoephedrine as a Practical Chiral Auxiliary for the Synthesis of Highly Enantiomerically Enriched CarboxylicAcids, Alcohols, Aldehydes, and Ketones, J. Am. Chem. Soc., 1997, 6496-6511, 119.
Baxter, Anthony et al, Synthesis and Use of 7-Substituted Norbornadienes for The Preparation of Prostaglandins and Prostanoids, J. Chem. Soc. Perkin Trans., 1986, 889-900, 1.
Drug Treatment of Glaucoma, Frontiers in Glaucoma, 2006, p. 26(144)-33(151). (Partial Translation—p. 26, right col. line 1 to p. 27 left col., line 3), vol. 7, No. 3.
Drug Treatment of Glaucoma, Frontiers in Glaucoma, 2006, pp. 26 (144)-33 (151)—Full Translation, vol. 7, No. 3.
Drysdale, Martin et al, Rationally Designed "Dipeptoid" Analogues of CCK. Acid Mimics of the Potent and Slective non-Peptide CCK-B Receptor Antagonist CI-988, J Med Chem, 1992, 2573-2581, 35.
Francis A. Carey, Organic Chemistry, conformations of Alkanes and Cycloalkanes, 1987, 63, Chapter 3, McGraw-Hill Book Company, New York.

(Continued)

*Primary Examiner* — Taofiq A Solola
(74) *Attorney, Agent, or Firm* — Jonathan Bass

(57) ABSTRACT

Disclosed herein is a compound of the formula

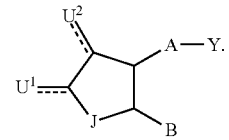

Therapeutic methods, compositions, and medicaments, related thereto are also disclosed.

7 Claims, No Drawings

(56) References Cited

OTHER PUBLICATIONS

Furrow et al, Practical Procedures for the Preparation of N-tert-Butyldimethylsilylhydrazones and Their Use in Modified Wolff-Kishner Reductions and in the Synthesis of Vinyl Halides and gem-Dihalides, JACS, 2004, 5436-5445, 126.
Han, Wei et al, Investigation of Glycine a-Ketoamide HCV NS3 Protease Inhibitors: Effect of Carboxylic Acid Isosteres, Bioorganic & Medicinal Chemistry Letters, 2005, 3487-3490, 15.
International Search Report & Written Opinion mailed on Jun. 16, 2008 for PCT/US08/51568 filed on Jan. 21, 2008 in the name of Allergan, Inc.
Kohara, Yasuhisa et al, Synthesis and Angiotensin II Receptor Antagonistic Activities of Benzimidazole Derivatives Bearing Acidic Heterocycles as Novel Tetrazole Bioisosteres, J Med Chem, 1996, 5228-5235, 39.
Orlek, Barry et al, Comparison of Azabicyclic Esters and Oxadiazoles as Ligands for the Muscarinic Receptor, J Med Chem, 1991, 2726-2735, 34.
Richard B. Silverman, Lead Modification: Drug Design and Development, The Organic Chemistry of Drugs, 2004, 29-45, N/A.
Tius, Marcus A., The Reaction of XeF2 with Trialkylvinyistannanes: Scope and Some Mechanistic Observations, Tetrahedron, 1995, 3997-4010, 51 (14).
Anderson, KE, et al., Oxadiazoles as bioisosteric transformations of carboxlic functionalities. II, Eur. J. Med. Chem. 1996, 31: 417-425.

SUBSTITUTED ARYLCYCLOPENTENES AS THERAPEUTIC AGENTS

CROSS-REFERENCE

This application is a continuation of U.S. application Ser. No. 14/273,114, filed May 8, 2014, which is a continuation of U.S. application Ser. No. 12/524,305, filed Feb. 1, 2010, now U.S. Pat. No. 8,722,726, issued May 13, 2014, which is a national phase application under 35 U.S.C. §371 of PCT Patent Application No. PCT/US2008/051568, filed Jan. 21, 2008, which claims the benefit of U.S. Application Ser. No. 60/886,533, filed Jan. 25, 2007, the disclosures of which are hereby incorporated by reference in their entireties and serve as the basis of a priority and/or benefit claim for the present application.

DESCRIPTION OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

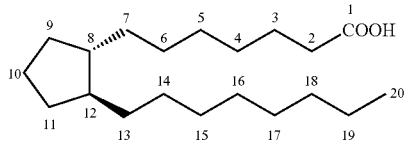

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Disclosed herein is a compound of the formula

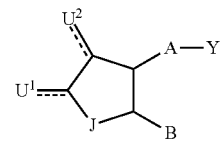

or a pharmaceutically acceptable salt thereof, or a prodrug thereof;

wherein a dashed line represents the presence or absence of a bond;

Y is an organic acid functional group, or an amide or ester thereof comprising up to 14 carbon atoms; or Y is hydroxymethyl or an ether thereof comprising up to 14 carbon atoms; or Y is a tetrazolyl functional group;

A is —$(CH_2)_6$—, cis —$CH_2CH=CH—(CH_2)_3$—, or —$CH_2C\equiv C—(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$ may be replaced by —CH=CH— or C≡C;

$U^1$ and $U^2$ are independently H, O; OH, I, Br, Cl, F, $CF_3$, CN, or $CH_2OH$;

J is

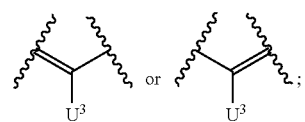

$U^3$ is H, OH, I, Br, Cl, F, CN, $C_{1-6}$ alkyl, aryl, heteroaryl, or $C_{1-6}$ hydroxyalkyl; and B is aryl or heteroaryl.

Also disclosed is a compound of the formula

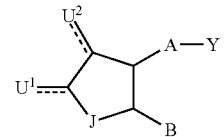

or a pharmaceutically acceptable salt thereof, or a prodrug thereof;
wherein a dashed line represents the presence or absence of a bond;
Y is carboxylic acid or a bioisostere thereof;
A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced by S or O; or A is —(CH$_2$)$_m$—Ar—(CH$_2$)$_o$— wherein Ar is interarylene or heterointerarylene, the sum of m and o is 1, 2, 3, or 4, and wherein 1 —CH$_2$— may be replaced by S or O, and 1 —CH$_2$—CH$_2$ may be replaced by —CH=CH— or C≡C;
U$^1$ and U$^2$ are independently H, O; OH, I, Br, Cl, F, CF$_3$, CN, or CH$_2$OH;
J is

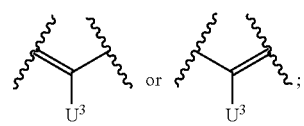

U$^3$ is H, OH, I, Br, Cl, F, CN, C$_{1-6}$ alkyl, aryl, heteroaryl, or C$_{1-6}$ hydroxyalkyl; and
B is aryl or heteroaryl.

These compounds are useful for treating glaucoma or ocular hypertension.

The definitions, explanations, and examples provided in this document shall be used to determine the meaning of a particular term or expression where there is any ambiguity arising from any disclosure incorporated by reference herein.

"Bioisosteres are substituents or groups that have chemical or physical similarities, and which produce broadly similar biological properties." Silverman, Richard B., *The Organic Chemistry of Drug Design and Drug Action*, 2$^{nd}$ Edition, Amsterdam: Elsevier Academic Press, 2004, p. 29.

While not intending to be limiting, organic acid functional groups are bioisoteres of carboxylic acids. An organic acid functional group is an acidic functional group on an organic molecule. While not intending to be limiting, organic acid functional groups may comprise an oxide of carbon, sulfur, or phosphorous. Thus, while not intending to limit the scope of the invention in any way, in certain compounds Y is a carboxylic acid, sulfonic acid, or phosphonic acid functional group.

Additionally, an amide or ester of one of the organic acids mentioned above comprising up to 14 carbon atoms is also contemplated for Y. In an ester, a hydrocarbyl moiety replaces a hydrogen atom of an acid such as in a carboxylic acid ester, e.g. CO$_2$Me, CO$_2$Et, etc.

In an amide, an amine group replaces an OH of the acid. Examples of amides include CON(R$^2$)$_2$, CON(OR$^2$)R$^2$, CON(CH$_2$CH$_2$OH)$_2$, and CONH(CH$_2$CH$_2$OH) where R$^2$ is independently H, C$_1$-C$_6$ alkyl, phenyl, or biphenyl. Moieties such as CONHSO$_2$R$^2$ are also amides of the carboxylic acid notwithstanding the fact that they may also be considered to be amides of the sulfonic acid R$^2$—SO$_3$H. The following amides are also specifically contemplated, CONSO$_2$-biphenyl, CONSO$_2$-phenyl, CONSO$_2$-heteroaryl, and CONSO$_2$-naphthyl. The biphenyl, phenyl, heteroaryl, or naphthyl may be substituted or unsubstituted.

Han et. al. (Biorganic & Medicinal Chemistry Letters 15 (2005) 3487-3490) has recently shown that the groups shown below are suitable bioisosteres for a carboxylic acid. The activity of compounds with these groups in inhibiting HCV NS3 protease was comparable to or superior to similar compounds where the group is replaced by CO$_2$H. Thus, Y could be any group depicted below.

Carboxylic Acid Bioisosteres According to Han et. al.

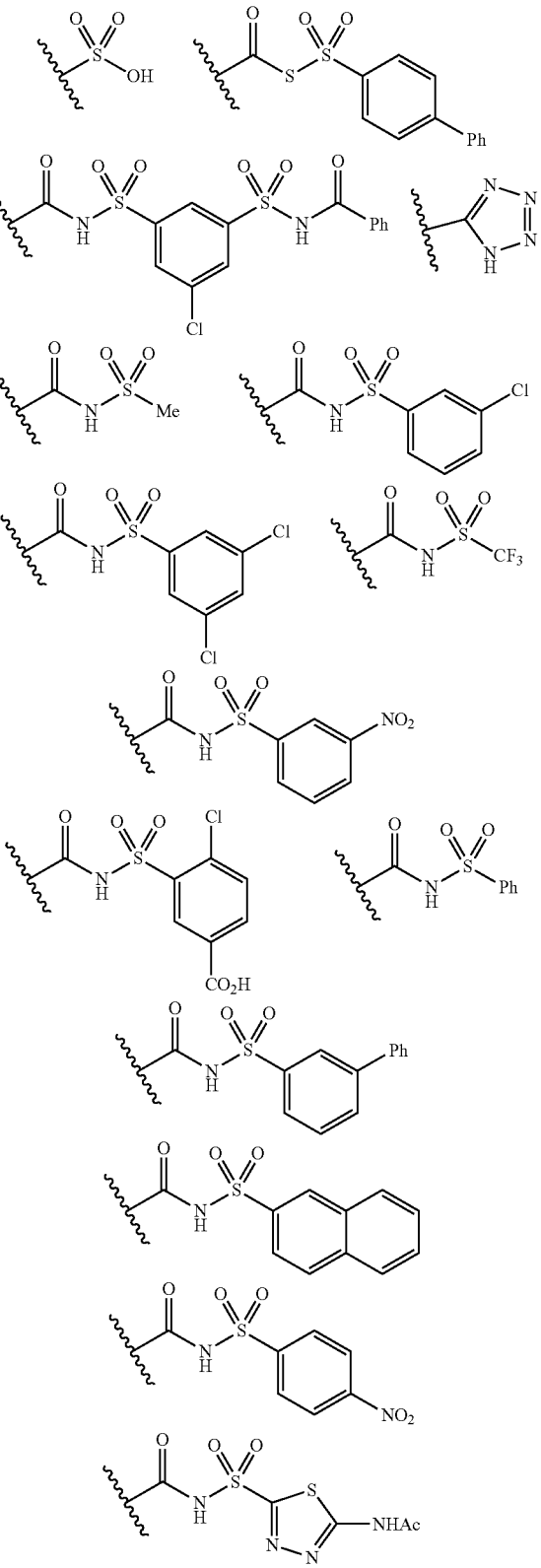

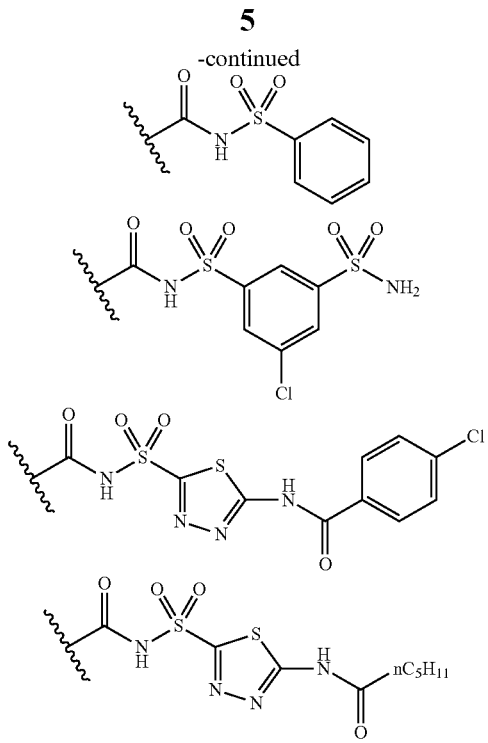

While not intending to limit the scope of the invention in any way, Y may also be hydroxymethyl or an ether thereof comprising up to 14 carbon atoms. An ether is a functional group wherein a hydrogen of an hydroxyl is replaced by carbon, e.g., Y is $CH_2OCH_3$, $CH_2OCH_2CH_3$, etc. These groups are also bioisosteres of a carboxylic acid.

"Up to 14 carbon atoms" means that the entire Y moiety, including the carbonyl carbon of a carboxylic acid ester or amide, and both carbon atoms in the —$CH_2O$—C of an ether has 0, 1, 2, 3, 4, 5, 6, 7, 8, 9, 10, 11, 12, 13, or 14 carbon atoms.

Finally, while not intending to limit the scope of the invention in any way, Y may be a tetrazolyl functional group.

Thus, while not intending to be limiting, the structures below exemplify what is meant by tetrazolyl; carboxylic acid, phosphonic acid, sulfonic acid, and their esters and amides; hydroxymethyl and ether of hydroxymethyl. In these structures, R is H or hydrocarbyl, subject to the constraints defined herein.

Each structure below represents a specific embodiment which is individually contemplated, as well as pharmaceutically acceptable salts and prodrugs of compounds which are represented by the structures.

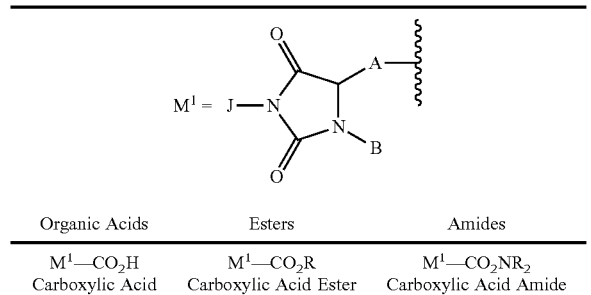

| Organic Acids | Esters | Amides |
|---|---|---|
| $M^1$—$CO_2H$ Carboxylic Acid | $M^1$—$CO_2R$ Carboxylic Acid Ester | $M^1$—$CO_2NR_2$ Carboxylic Acid Amide |
| $M^1$—$P(O)(OH)_2$ Phosphonic Acid | $M^1$—$P(O)(OH)OR$ Phosphoic Acid Ester | $M^1$—$P(O)(OH)NR_2$ Phosphonic Acid Amide |

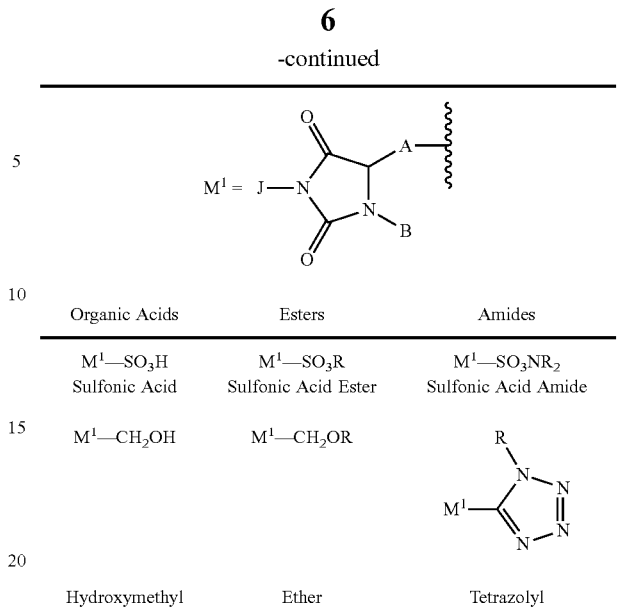

| Organic Acids | Esters | Amides |
|---|---|---|
| $M^1$—$SO_3H$ Sulfonic Acid | $M^1$—$SO_3R$ Sulfonic Acid Ester | $M^1$—$SO_3NR_2$ Sulfonic Acid Amide |
| $M^1$—$CH_2OH$ Hydroxymethyl | $M^1$—$CH_2OR$ Ether | Tetrazolyl |

A tetrazolyl functional group is another bioisostere of a carboxylic acid. An unsubstituted tetrazolyl functional group has two tautomeric forms, which can rapidly interconvert in aqueous or biological media, and are thus equivalent to one another. These tautomers are shown below.

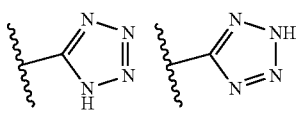

Additionally, if $R^2$ is $C_1$-$C_6$ alkyl, phenyl, or biphenyl, other isomeric forms of the tetrazolyl functional group such as the one shown below are also possible, unsubstituted and hydrocarbyl substituted tetrazolyl up to $C_{12}$ are considered to be within the scope of the term "tetrazolyl."

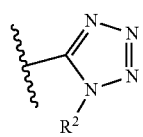

While not intending to limit the scope of the invention in any way, in one embodiment, Y is $CO_2R^2$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$,

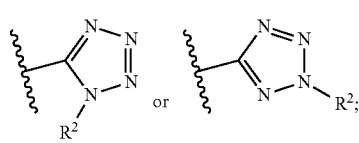

wherein $R^2$ is independently H, $C_1$-$C_6$ alkyl, unsubstituted phenyl, or unsubstituted biphenyl.

According to Silverman (p. 30), the moieties shown below are also bioisosteres of a carboxylic acid.

Carboxylic Acid Bioisosteres According to Silverman

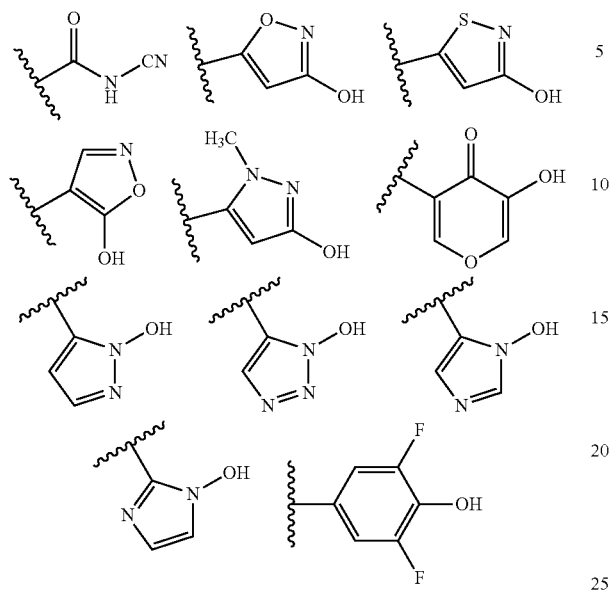

Orlek et al. (*J. Med. Chem.* 1991, 34, 2726-2735) described oxadiazoles as suitable bioisosteres for a carboxylic acid. These ester replacements were shown to be potent muscarinic agonists having improved metabolic stability. Oxadiazoles were also described by Anderson et al. (Eur. J. Med. Chem. 1996, 31, 417-425) as carboxamide replacements having improved in vivo efficacy at the benzodiazepine receptor.

Carboxylic Acid Bioisosteres According to Orlek et. al.

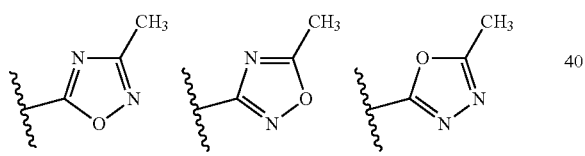

Kohara et al. (*J. Med. Chem.* 1996, 39, 5228-5235) described acidic heterocycles as suitable bioisosteres for a tetrazole. These carboxylic acid replacements were shown to be potent angiotensin II receptor antagonists having improved metabolic stability.

Tetrazole Bioisosteres According to Kohara et. al.

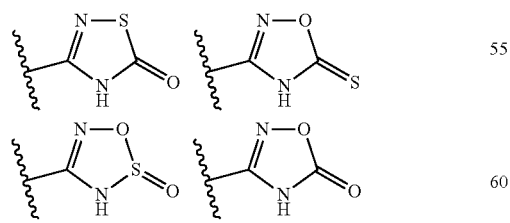

Drysdale et al. (*J. Med. Chem.* 1992, 35, 2573-2581) have described carboxylic acid mimics of non-peptide CCK-B receptor antagonists. The binding affinities of many of the bioisosteres are similar to the parent carboxylic acid.

Carboxylic Acid Bioisosteres According to Drysdale et. al.

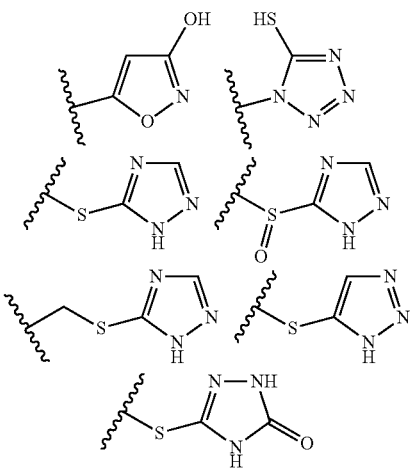

A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be replaced by S or O; or A is —(CH$_2$)$_m$—Ar—(CH$_2$)$_o$— wherein Ar is interarylene or heterointerarylene, the sum of m and o is 1, 2, 3, or 4, and wherein 1 —CH$_2$— may be replaced by S or O, and 1 —CH$_2$—CH$_2$ may be replaced by —CH═CH— or C≡C—.

Thus, while not intending to be limiting, A may be —(CH$_2$)$_6$—, cis —CH$_2$CH═CH—(CH$_2$)$_3$—, or —CH$_2$C≡C—(CH$_2$)$_3$—.

Alternatively, A may be a group which is related to one of these three moieties in that any carbon is replaced with S or O. For example, while not intending to limit the scope of the invention in any way, A may be a moiety where S replaces one or two carbon atoms such as one of the following or the like.

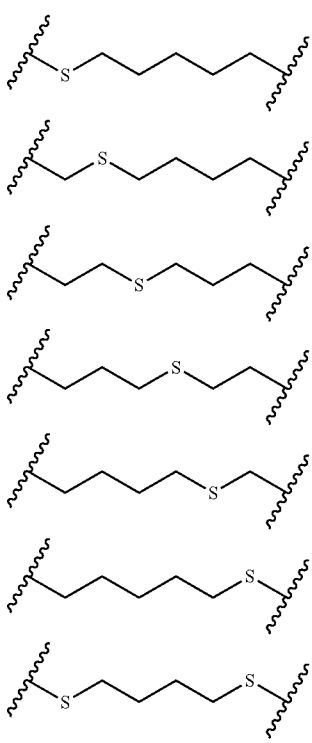

-continued

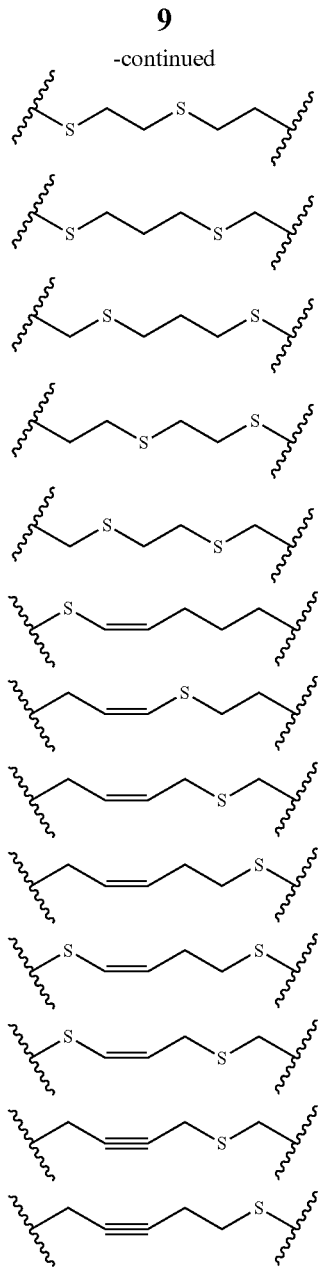

Alternatively, while not intending to limit the scope of the invention in any way, A may be a moiety where O replaces one or two carbon atoms such as one of the following or the like.

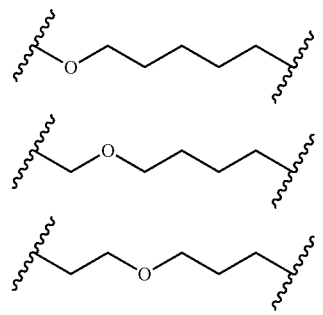

-continued

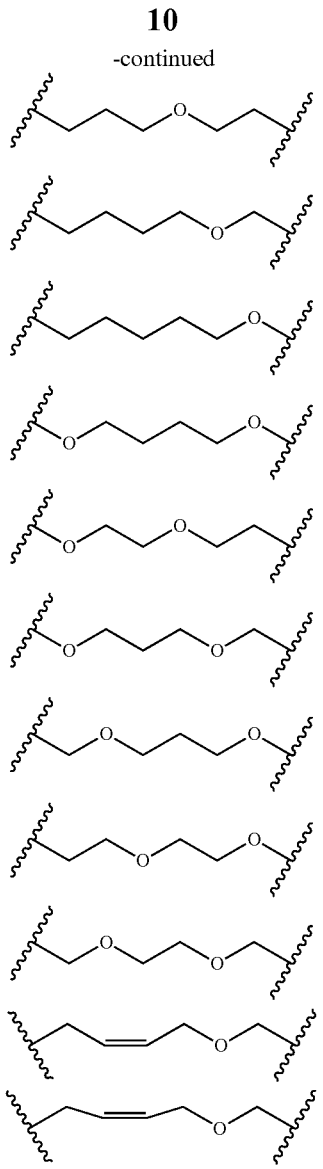

Alternatively, while not intending to limit the scope of the invention in any way, A may have an O replacing one carbon atom and an S replacing another carbon atom, such as one of the following or the like.

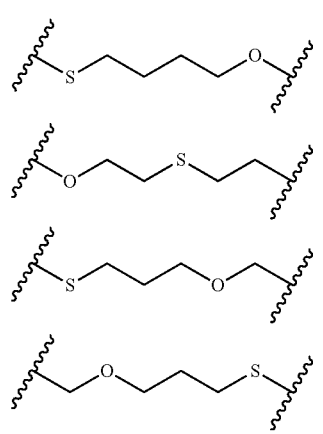

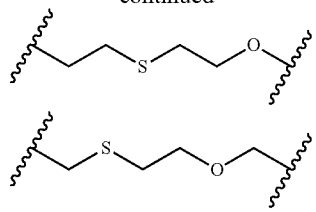

Alternatively, while not intending to limit the scope of the invention in any way, in certain embodiments A is —(CH$_2$)$_m$—Ar—(CH$_2$)$_o$— wherein Ar is interarylene or heterointerarylene, the sum of m and o is 1, 2, 3, or 4, and wherein 1 —CH$_2$— may be replaced by S or O and 1 —CH$_2$—CH$_2$ may be replaced by —CH=CH— or —C≡C—. In other words, while not intending to limit the scope of the invention in any way, in one embodiment A comprises:
1) a) 1, 2, 3, or 4 CH$_2$ moieties, or
  b) 0, 1 or 2 CH$_2$ moieties and —CH=CH— or —C≡C—; and
2) Ar;
e.g. —CH$_2$—Ar—, —(CH$_2$)$_2$—Ar—, —CH=CH—Ar—, —CH$_2$—Ar—CH$_2$—, —CH$_2$Ar—(CH$_2$)$_2$—, —CH$_2$Ar—CH=CH—, —CH$_2$Ar—C≡C—, —(CH$_2$)$_2$—Ar—(CH$_2$)$_2$—, and the like;

in another embodiment A comprises:
1) a) O; and 0, 1, 2, or 3 CH$_2$ moieties; or
  b) O; and 0 or 1 CH$_2$ moieties and —CH=CH— or —C≡C—; and
2) Ar;
e.g., —O—Ar—, Ar—CH$_2$—O—, —O—Ar—(CH$_2$)$_2$—, —OAr—CH=CH—, —O—Ar—C≡C—, —O—CH$_2$—Ar—, —O—CH$_2$—Ar—(CH$_2$)$_2$, —O—CH$_2$Ar—CH=CH—, —O—CH$_2$Ar—C≡C—, and the like; or in another embodiment A comprises:
1) a) S; and 0, 1, 2, or 3 CH$_2$ moieties; or
  b) S; and 0 or 1 CH$_2$ moieties and —CH=CH— or —C≡C—; and
2) Ar;
e.g., —S—Ar—, Ar—CH$_2$—S—, —S—Ar—(CH$_2$)$_2$—, —SAr—CH=CH—, —S—Ar—C≡C—, —S—CH$_2$—Ar—, —S—CH$_2$—Ar—(CH$_2$)$_2$, —S—CH$_2$Ar—CH=CH—, —S—CH$_2$Ar—C≡C—, and the like.

In another embodiment, the sum of m and o is 2, 3, or 4 wherein one CH$_2$ may be replaced with S or O and 1 —CH$_2$—CH$_2$ may be replaced by —CH=CH— or —C≡C—.

In another embodiment, the sum of m and o is 3 wherein one CH$_2$ may be replaced with S or O and 1 —CH$_2$—CH$_2$ may be replaced by —CH=CH— or —C≡C—.

In another embodiment, the sum of m and o is 2 wherein one CH$_2$ may be replaced with S or O or 1 —CH$_2$—CH$_2$ may be replaced by —CH=CH— or C≡C—.

In another embodiment, the sum of m and o is 4 wherein one CH$_2$ may be replaced with S or O and 1 —CH$_2$—CH$_2$ may be replaced by —CH=CH— or —C≡C—.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —(CH$_2$)$_2$-Ph-. While not intending to limit scope of the invention in any way, substituents may have 4 or less heavy atoms, wherein the heavy atoms are C, N, O, S, P, F, Cl, Br, and/or I in any stable combination. Any number of hydrogen atoms required for a particular substituent will also be included. In addition to the atoms listed above, a substituent may also have a metal cation or any other stable cation having an atom not listed above if the substituent is acidic and the salt form is stable. For example, —OH may form an —O$^-$Na$^+$ salt or CO$_2$H may form a CO$_2{}^-$K$^+$ salt. Any cation of the salt is not counted in the "4 or less heavy atoms." Thus, the substituent may be hydrocarbyl, i.e. a moiety consisting of only carbon and hydrogen, including linear, branched or cyclic hydrocarbyl, and combinations thereof; having up to 4 carbon atoms, including alkyl up to C$_4$, alkenyl, alkynyl, and the like;

hydrocarbyloxy, i.e. —O-hydrocarbyl, up to C$_3$;

organic acid such as CO$_2$H, SO$_3$H, P(O)(OH)$_2$, and the like, and salts thereof;

CF$_3$;

halo, such as F, Cl, or Br;

hydroxyl;

NH$_2$ and alkylamine functional groups up to C$_3$;

other N or S containing substituents such as CN, NO$_2$, and the like;

and the like.

In one embodiment A is —(CH$_2$)$_m$-Ph-(CH$_2$)$_o$— wherein the sum of m and o is 1, 2, or 3, and wherein one CH$_2$ may be replaced with S or O.

In another embodiment A is —CH$_2$—Ar—OCH$_2$—. In another embodiment A is —CH$_2$-Ph-OCH$_2$—. In another embodiment, Ph is attached at the 1 and 3 positions, otherwise known as m-interphenylene, such as when A has the structure shown below.

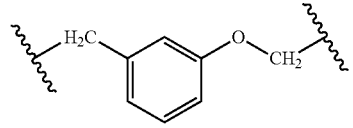 [SMILES: *COc1cccc(C*)c1]

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph- wherein one CH$_2$ may be replaced with S or O.

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph-.

In one embodiment, Ar is thienyl.

In other embodiments, A has one of the following structures.

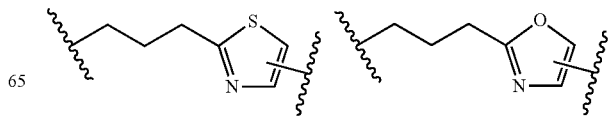

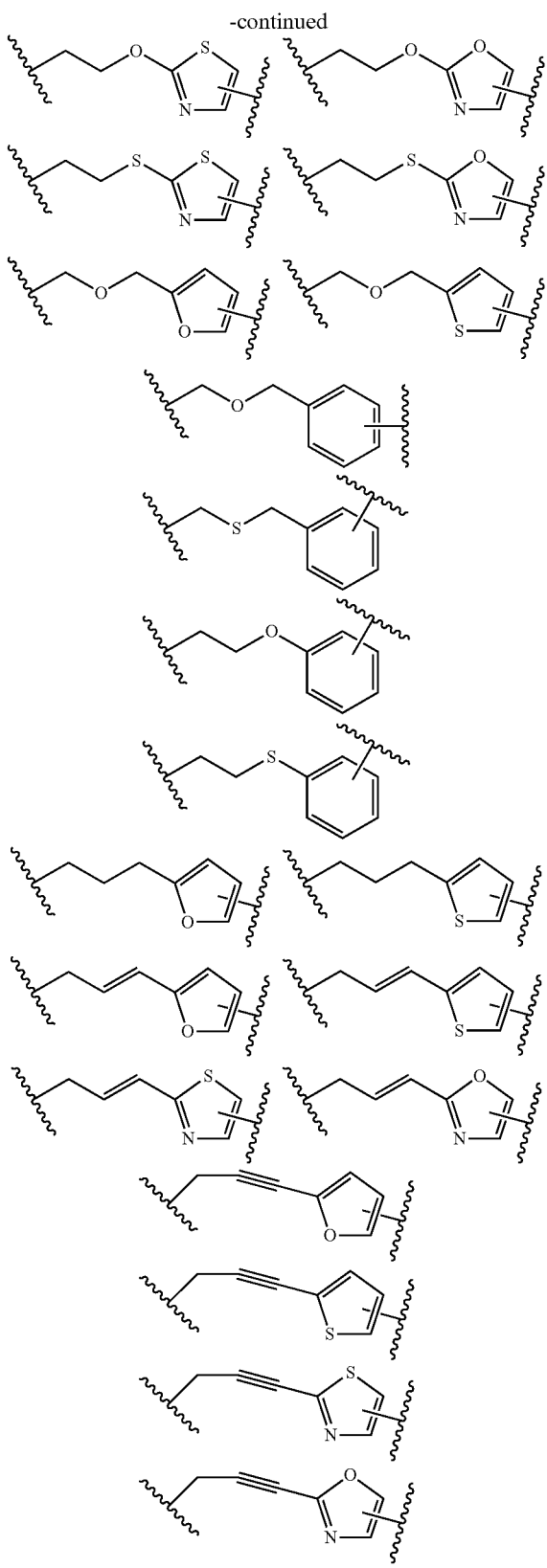

In another embodiment A is —CH₂OCH₂Ar.
In another embodiment A is —CH₂SCH₂Ar.
In another embodiment A is —(CH₂)₃Ar.
In another embodiment A is —CH₂O(CH₂)₄.

In another embodiment A is —CH₂S(CH₂)₄.
In another embodiment A is —(CH₂)₆—.
In another embodiment A is cis —CH₂CH=CH—(CH₂)₃—.
In another embodiment A is —CH₂C≡C—(CH₂)₃—.
In another embodiment A is —S(CH₂)₃S(CH₂)₂—.
In another embodiment A is —(CH₂)₄OCH₂—.
In another embodiment A is cis —CH₂CH=CH—CH₂OCH₂—.
In another embodiment A is —CH₂CH≡CH—CH₂OCH₂—.
In another embodiment A is —(CH₂)₂S(CH₂)₃—.
In another embodiment A is —CH₂-Ph-OCH₂—, wherein Ph is interphenylene.
In another embodiment A is —CH₂-mPh-OCH₂—, wherein mPh is m-interphenylene.
In another embodiment A is —CH₂—O—(CH2)₄-.
In another embodiment A is —CH₂—O—CH₂—Ar—, wherein Ar is 2,5-interthienylene.
In another embodiment A is —CH₂—O—CH₂—Ar—, wherein Ar is 2,5-interfurylene.
In another embodiment A is (3-methylphenoxy)methyl.
In another embodiment A is (4-but-2-ynyloxy)methyl.
In another embodiment A is 2-(2-ethylthio)thiazol-4-yl.
In another embodiment A is 2-(3-propyl)thiazol-5-yl.
In another embodiment A is 3-(methoxymethyl)phenyl.
In another embodiment A is 3-(3-propylphenyl).
In another embodiment A is 3-methylphenethyl.
In another embodiment A is 4-(2-ethyl)phenyl.
In another embodiment A is 4-phenethyl.
In another embodiment A is 4-methoxybutyl.
In another embodiment A is 5-(methoxymethyl)furan-2-yl.
In another embodiment A is 5-(methoxymethyl)thiophen-2-yl.
In another embodiment A is 5-(3-propyl)furan-2-yl.
In another embodiment A is 5-(3-propyl)thiophen-2-yl.
In another embodiment A is 6-hexyl.
In another embodiment A is (Z)-6-hex-4-enyl.

U¹ is H, O; OH, I, Br, Cl, F, CF₃, CN, or CH₂OH. Thus, the structures below are possible. Each structure below represents a specific embodiment which is individually contemplated, as well as pharmaceutically acceptable salts and prodrugs of compounds which are represented by the structures.

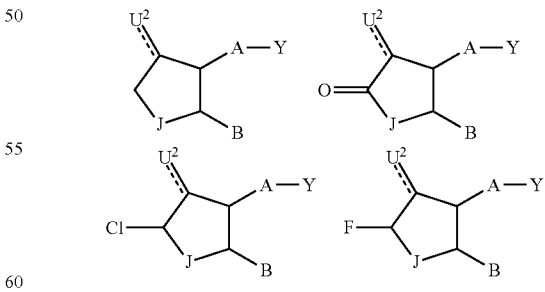

U² is H, O; OH, I, Br, Cl, F, CF₃, CN, or CH₂OH. Thus, the structures below are possible. Each structure below represents a specific embodiment which is individually contemplated, as well as pharmaceutically acceptable salts and prodrugs of compounds which are represented by the structures.

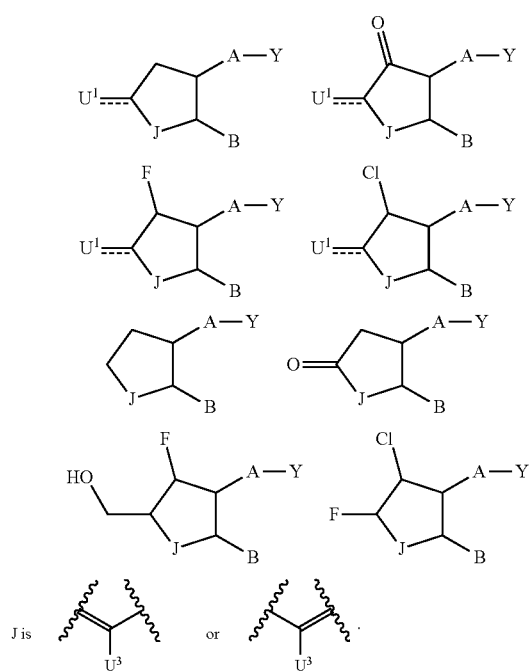

Thus, the structures below are possible. Each structure below represents a specific embodiment which is individually contemplated, as well as pharmaceutically acceptable salts and prodrugs of compounds which are represented by the structures.

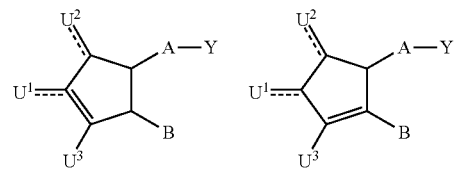

$U^3$ is H, OH, I, Br, Cl, F, CN, $C_{1-6}$ alkyl, aryl, or heteroaryl, or $C_{1-6}$ hydroxyalkyl. Thus, the structures below are possible. Each structure below represents a specific embodiment which is individually contemplated, as well as pharmaceutically acceptable salts and prodrugs of compounds which are represented by the structures.

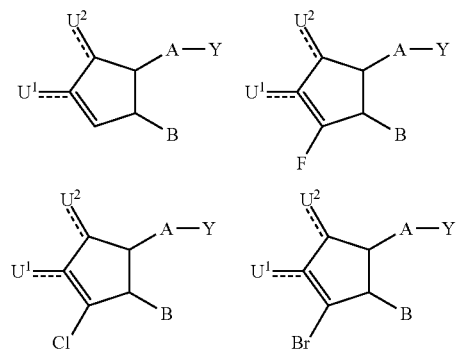

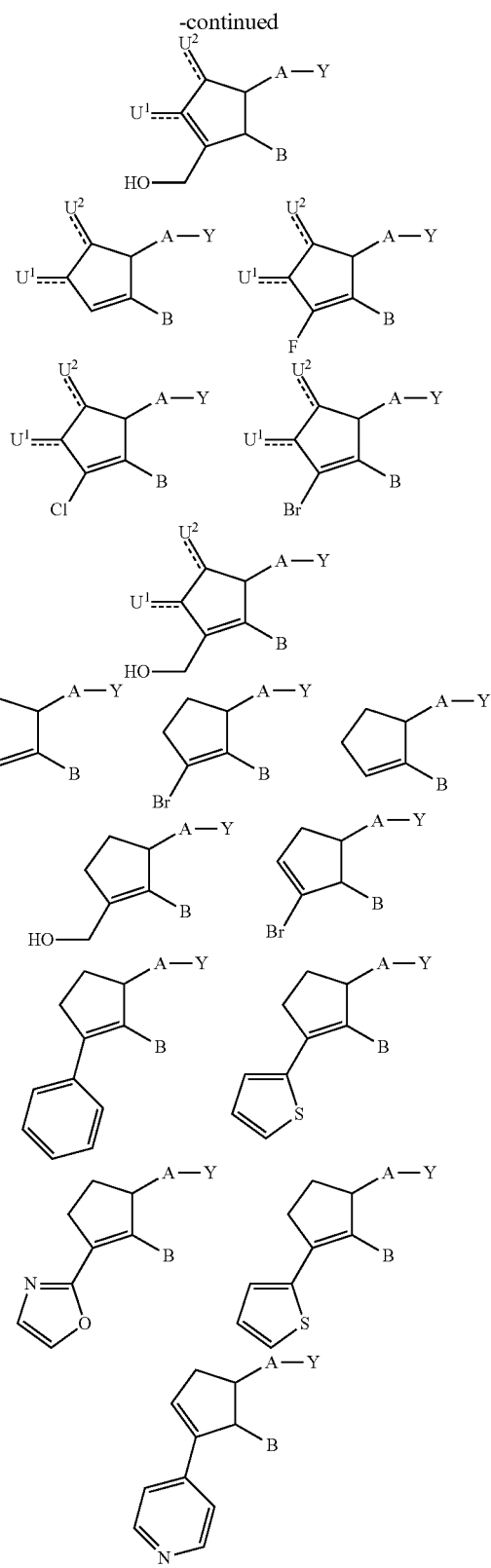

Aryl and heteroaryl with regard to $U^3$ is the same as that of B.

Compounds according to either of the two tautomeric forms shown below are also contemplated. For any structure depicted herein, any tautomer or tautomeric forms of the compound depicted by the structure are considered to be included in compounds of that structure.

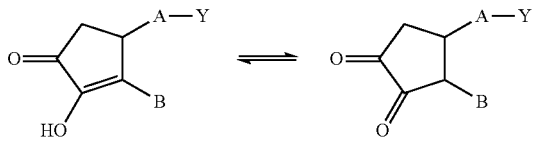

Thus, if the structure on the left is depicted herein, it is intended to cover the tautomer depicted on the right and any other tautomers or tautomeric forms that may exist.

B is aryl or heteroaryl.

Aryl is an aromatic ring or ring system such as phenyl, naphthyl, biphenyl, and the like.

Heteroaryl is aryl having one or more N, O, or S atoms in the ring, i.e. one or more ring carbons are substituted by N, O, and/or S. While not intending to be limiting, examples of heteroaryl include thienyl, pyridinyl, furyl, benzothienyl, benzofuryl, imidizololyl, indolyl, and the like.

A substituent of aryl or heteroaryl should be stable and may have up to 20 non-hydrogen atoms each and as many hydrogen atoms as necessary, wherein the non-hydrogen atoms are C, N, O, S, P, F, Cl, Br, and/or I in any stable combination. However, the total number of non-hydrogen atoms on all of the substituents combined must also be 20 or less. In addition to the atoms listed above, a substituent may also have a metal cation or other stable cation having an atom not listed above if the substituent is acidic and the salt form is stable. For example, —OH may form an —O$^-$Na$^+$ salt or $CO_2H$ may form a $CO_2^-K^+$ salt. Any cation of the salt is not counted in the 20 non-hydrogen atoms. Thus, while not intending to limit the scope of the invention in any way, a substituent may be:

hydrocarbyl, i.e. a moiety consisting of only carbon and hydrogen such as alkyl, alkenyl, alkynyl, and the like, including linear, branched or cyclic hydrocarbyl, and combinations thereof;

hydrocarbyloxy, meaning O-hydrocarbyl such as $OCH_3$, $OCH_2CH_3$, O-cyclohexyl, etc, up to 19 carbon atoms; other ether substituents such as $CH_2OCH_3$, $(CH_2)_2OCH(CH_3)_2$, and the like; thioether substituents including S-hydrocarbyl and other thioether substituents;

hydroxyhydrocarbyl, meaning hydrocarbyl-OH, including hydroxyalkyl, such as $CH_2OH$, $C(CH_3)_2OH$, etc, up to 19 carbon atoms;

nitrogen substituents such as $NO_2$, CN, and the like, including amino, such as $NH_2$, $NH(CH_2CH_3OH)$, $NHCH_3$, and the like;

carbonyl substituents, such as $CO_2H$, ester, amide, and the like;

halogen, such as chloro, fluoro, bromo, and the like fluorocarbyl, such as $CF_3$, $CF_2CF_3$, etc.;

phosphorous substituents, such as $PO_3^{2-}$, and the like;

sulfur substituents, including S-hydrocarbyl, SH, $SO_3H$, $SO_2$-hydrocarbyl, $SO_3$-hydrocarbyl, and the like.

Substituted aryl or heteroaryl may have as many substituents as the ring or ring system will bear, and the substituents may be the same or different. Thus, for example, an aryl ring or a heteroaryl ring may be substituted with chloro and methyl; methyl, OH, and F; CN, $NO_2$, and ethyl; and the like including any conceivable substituent or combination of substituent possible in light of this disclosure.

Substituted aryl or substituted heteroaryl also includes a bicyclic or polycyclic ring system wherein one or more rings are aromatic and one or more rings are not. For example, indanonyl, indanyl, indanolyl, tetralonyl, and the like are substituted aryl and are also substituted phenyl. For this type of polycyclic ring system, an aromatic or heteroaromatic ring, not a non-aromatic ring, must be attached to the remainder of the molecule, i.e. the part of the molecule that is not B. In other words, in any structure depicting —B herein, where — is a bond, the bond is a direct bond to an aromatic ring.

Hydrocarbyl is a moiety consisting of carbon and hydrogen, including, but not limited to:

1. alkyl, which is hydrocarbyl containing no double or triple carbon-carbon bonds; alkyl includes, but is not limited to:
   linear alkyl, cyclic alkyl, branched alkyl, and combinations thereof;
   $C_{1-3}$ alkyl, which refers to alkyl having 1, 2, or 3 carbon atoms, including, but no limited to, methyl, ethyl, isopropyl, cyclopropyl, n-propyl, and the like;
   $C_{1-6}$ alkyl, which refers to alkyl having 1, 2, 3, 4, 5, or 6 carbon atoms; including, but not limited to methyl, ethyl, propyl isomers, cyclopropyl, butyl isomers, cyclobutyl, pentyl isomers, cyclopentyl, hexyl isomers, cyclohexyl, and the like;
   combinations of these terms are possible, and their meanings should be obvious to those of ordinary skill in the art; for example $C_{1-6}$ linear alkyl would refer to $C_{1-6}$ alkyl which is also linear;
2. alkenyl, which is hydrocarbyl containing one or more carbon-carbon double bonds; alkenyl includes, but is not limited to:
   linear alkenyl, cyclic alkenyl, branched alkenyl, and combinations thereof;
   alkenyl having 1, 2, 3, or more carbon-carbon double bonds;
3. alkynyl, which is hydrocarbyl containing one or more carbon-carbon triple bonds; akynyl includes, but is not limited to:
   linear alkynyl, cyclic alkynyl, branched alkynyl, and combinations thereof;
   alkynyl having 1, 2, 3, or more carbon-carbon double bonds;
4. aryl, provided that it contains no heteroatoms either in a ring or as a substituent; and
5. combinations of any of the above; $C_{1-6}$ hydroxyalkyl is hydroxyalkyl having 1, 2, 3, 4, 5, or 6 carbon atoms.

In another embodiment, B is substituted or unsubstituted phenyl.

In another embodiment, B is substituted or unsubstituted thienyl.

In another embodiment, B is substituted or unsubstituted naphthyl.

In another embodiment, B is substituted or unsubstituted furyl.

In another embodiment, B is substituted or unsubstituted pyridinyl.

In another embodiment, B is substituted or unsubstituted benzothienyl.

In another embodiment, B is substituted or unsubstituted indanyl.

In another embodiment, B is substituted or unsubstituted tetralonyl.

In another embodiment, B has 1, 2, 3, 4, or 5 substituents, wherein each substituent has one or more carbon, fluorine, chlorine, bromine, oxygen, sulfur, or atoms; and wherein all substituents taken together consist of 0, 1, 2, 3, 4, 5, 6, 7, 8, 9 or 10 carbon atoms; 0, 1, 2, 3, 4, 5, 6, 7, 8 or 9 fluorine atoms; 0, 1, 2 or 3 chlorine atoms, 0, 1, 2 or 3 bromine atoms, 0, 1, 2 or 3 oxygen atoms; 0, 1, 2, or 3 sulfur atoms; 0, 1, 2, or 3 nitrogen atoms; and from 0 to 24 hydrogen atoms.

In another embodiment, B has 1, 2, 3, 4, or 5 substituents, wherein each substituent has one or more carbon, fluorine, chlorine, bromine, or oxygen atoms; and wherein all substituents taken together consist of 0, 1, 2, 3, 4, 5, 6, 7, 8, 9 or 10 carbon atoms; 0, 1, 2, 3, 4, 5, 6, 7, 8 or 9 fluorine atoms; 0, 1, 2 or 3 chlorine atoms, 0, 1, 2 or 3 bromine atoms; 0, 1, 2 or 3 oxygen atoms; and from 0 to 24 hydrogen atoms.

In another embodiment, B has a substituent of the formula $C_aH_bO_c$; wherein a is 0, 1, 2, 3, 4, 5, 6, 7, 8 or 9, b is 0, 1, 2, 3, 4, 5, 6, 7, 8, 9, 10, 11, 12, 13, 14, 15, 16, 17, 18 or 19; and c is 0, 1, 2, or 3.

In another embodiment, B has 1, 2, 3, or 4 alkyl substituents having 1, 2, 3, 4, 5, 6, 7, 8, 9 or 10 carbon atoms.

In another embodiment, B has a hydroxyalkyl substituent; said hydroxyalkyl substituent having 0, 1, 2, 3, 4, 5, 6, 7, 8, 9 or 10 carbon atoms and 1 or 2 hydroxy moieties.

In another embodiment, B has an alkyl substituent having 0, 1, 2, 3, 4, 5, 6, 7, 8, 9 or 10 carbon atoms.

Examples of useful moieties for B are depicted below. Each is individually contemplated as an embodiment.

Structure: 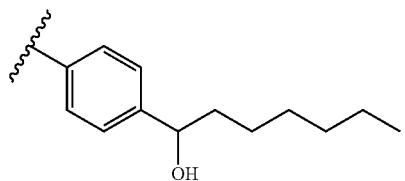 [SMILES: *c1ccc(C(O)CCCCCC)cc1] 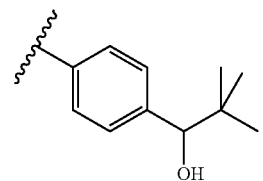 [SMILES: *c1ccc(C(O)C(C)(C)C)cc1]

Name: 4-(1-hydroxyheptyl)phenyl     4-(1-hydroxy-2,2-dimethylpropyl)phenyl

Structure: 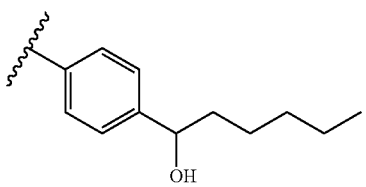 [SMILES: *c1ccc(C(O)CCCCC)cc1] 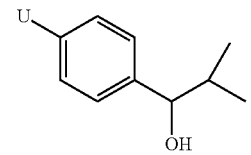

Name: 4-(1-hydroxyhexyl)phenyl     4-(1-hydroxy-2-methylpropyl)phenyl

Structure: 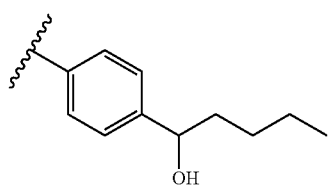 [SMILES: *c1ccc(C(O)CCCC)cc1] 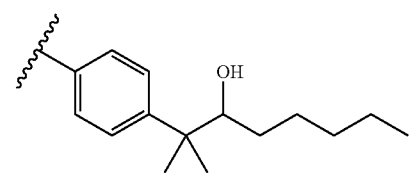 [SMILES: *c1ccc(C(C)(C)C(O)CCCCC)cc1]

Name: 4-(1-hydroxypentyl)phenyl     4-(3-hydroxy-2-methyloctan-2-yl)phenyl

Structure: 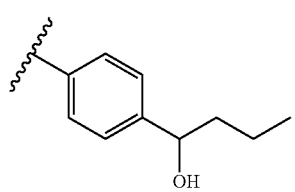 [SMILES: *c1ccc(C(O)CCC)cc1] 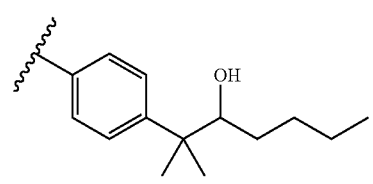 [SMILES: *c1ccc(C(C)(C)C(O)CCCC)cc1]

Name: 4-(1-hydroxybutyl)phenyl     4-(3-hydroxy-2-methylheptan-2-yl)phenyl

Structure: 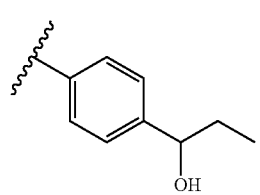 [SMILES: *c1ccc(C(O)CC)cc1] 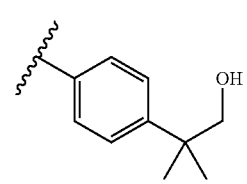 [SMILES: *c1ccc(C(C)(C)CO)cc1]

Name: 4-(1-hydroxypropyl)phenyl     4-(1-hydroxy-2-methylpropan-2-yl)phenyl

-continued

| Structure: | | |
|---|---|---|
| | 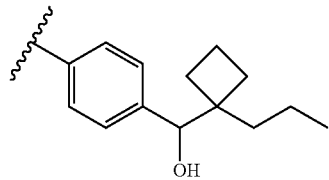 [SMILES: *c1ccc(C(O)C2(CCC)CCC2)cc1] | 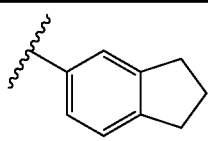 |
| Name: | 4-(hydroxy(1-propylcyclobutyl)methyl)phenyl | 2,3-dihydro-1H-inden-5-yl |
| Structure: | 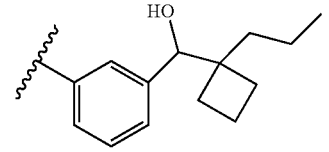 [SMILES: *c1cccc(C(O)C2(CCC)CCC2)c1] | 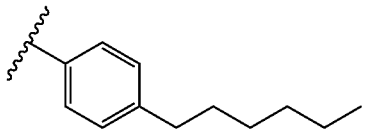 [SMILES: *c1ccc(CCCCCC)cc1] |
| Name: | 3-(hydroxy(1-propylcyclobutyl)methyl)phenyl | 4-hexylphenyl |
| Structure: | 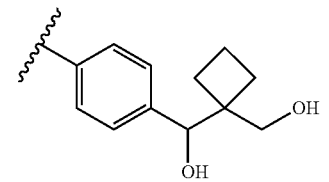 [SMILES: *c1ccc(C(O)C2(CO)CCC2)cc1] | 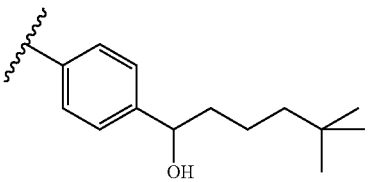 [SMILES: *c1ccc(C(O)CCCC(C)(C)C)cc1] |
| Name: | 4-(hydroxy(1-(hydroxymethyl)cyclobutyl)methyl)phenyl | 4-(1-hydroxy-5,5-dimethylhexyl)phenyl |
| Structure: | 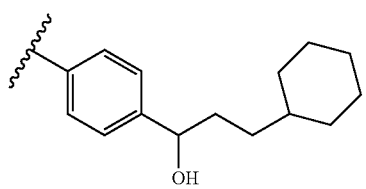 [SMILES: *c1ccc(C(O)CCC2CCCCC2)cc1] | 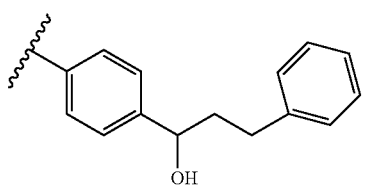 [SMILES: *c1ccc(C(O)CCc2ccccc2)cc1] |
| Name: | 4-(3-cyclohexyl-1-hydroxypropyl)phenyl | 4-(1-hydroxy-3-phenylpropyl)phenyl |
| Structure: | 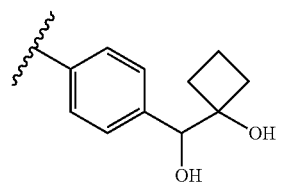 [SMILES: *c1ccc(C(O)C2(O)CCC2)cc1] | 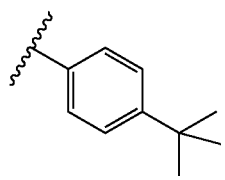 [SMILES: *c1ccc(C(C)(C)C)cc1] |
| Name: | 4-(hydroxy(1-hydroxycyclobutyl)methyl)phenyl | 4-tert-butylphenyl |
| Structure: | 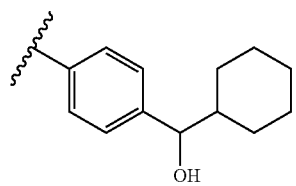 [SMILES: *c1ccc(C(O)C2CCCCC2)cc1] | 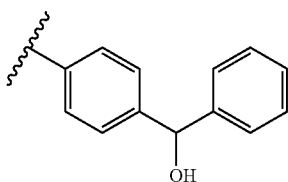 [SMILES: *c1ccc(C(O)c2ccccc2)cc1] |
| Name: | 4-(cyclohexyl(hydroxy)methyl)phenyl | 4-(hydroxy(phenyl)methyl)phenyl |
| Structure: | 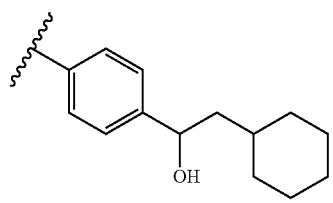 [SMILES: *c1ccc(C(O)CC2CCCCC2)cc1] | 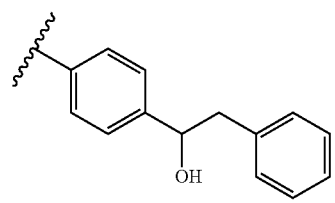 [SMILES: *c1ccc(C(O)Cc2ccccc2)cc1] |
| Name: | 4-(2-cyclohexyl-1-hydroxyethyl)phenyl | 4-(1-hydroxy-2-phenylethyl)phenyl |

-continued

| Structure: | 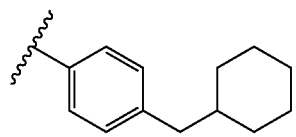 [SMILES: *c1ccc(CC2CCCCC2)cc1] | 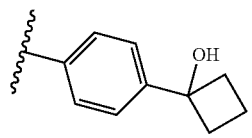 [SMILES: *c1ccc(C2(O)CCC2)cc1] |
|---|---|---|
| Name: | 4-(cyclohexylmethyl)phenyl | 4-(1-hydroxycyclobutyl)phenyl |
| Structure: | 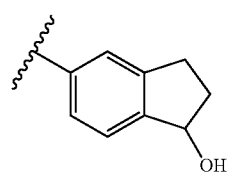 [SMILES: *c1ccc2c(c1)CCC2O] | 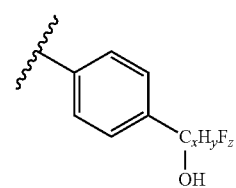 |
| Name: | 1-hydroxy-2,3-dihydro-1H-inden-5-yl | |
| Structure: | 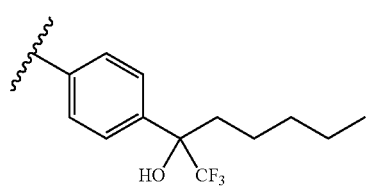 | 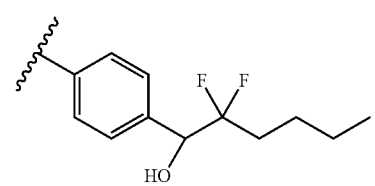 [SMILES: *c1ccc(C(O)C(F)(F)CCCC)cc1] |
| Name: | 4-(1,1,1-trifluoro-2-hydroxyheptan-2-yl)phenyl | 4-(2,2-difluoro-1-hydroxyhexyl)phenyl |

In the above embodiments, x is 5, 6, or 7, and y+z is 2x+1.

In one embodiment, x is 5 and y+z is 11.

In another embodiment, x is 6 and y+z is 13.

In another embodiment, x is 7 and y+z is 15.

A compound, substituent, moiety, or any structural feature is stable if it is sufficiently stable for the compound to be isolated for at least 12 hours at room temperature under normal atmospheric conditions, or if it is sufficiently stable to be useful for at least one use disclosed herein.

The term aromatic refers to the meaning commonly understood in the art, i.e. it refers to an unsaturated, fully conjugated ring having 4N+2 ring electrons (e.g. 2, 6, 10, etc.) Thus, phenyl, pyridinyl, thienyl, furyl, and the like are aromatic. Aryl is a moiety that is aromatic.

A heavy atom is an atom which is not hydrogen.

A heteroatom is an atom which is not carbon or hydrogen.

A pharmaceutically acceptable salt is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt. Examples of useful salts include, but are not limited to, sodium salts, potassium salts, calcium salts, ammonium salts and the like.

Unless otherwise indicated, reference to a compound should be construed broadly to include pharmaceutically acceptable salts, tautomers, and prodrugs of the depicted structure.

Unless stereochemistry is explicitly depicted, a structure is intended to include every possible stereoisomer, both pure or in any possible mixture. In particular, compounds having the stereochemistry indicated in the structures below are contemplated.

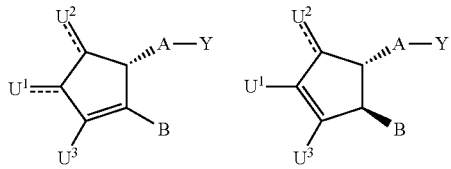

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge "represents a bond receding from the viewer."

For the purposes of this disclosure, "treat," "treating," or "treatment" refer to the use of a compound, composition, therapeutically active agent, or drug in the diagnosis, cure, mitigation, treatment, prevention of disease or other undesirable condition, or to affect the structure or any function of the body of man or other animals.

The compounds disclosed herein are useful in the manufacture of a medicament for the treatment of glaucoma or ocular hypertension in a mammal.

Another embodiment is a medicament comprising a compound disclosed herein, wherein said composition is a liquid which is ophthalmically acceptable.

Another embodiment is a method comprising administering a compound disclosed herein to a mammal for the treatment of glaucoma or ocular hypertension.

Another embodiment is a kit comprising a composition comprising compound disclosed herein, a container, and instructions for administration of said composition to a mammal for the treatment of glaucoma or ocular hypertension.

Synthetic Methods

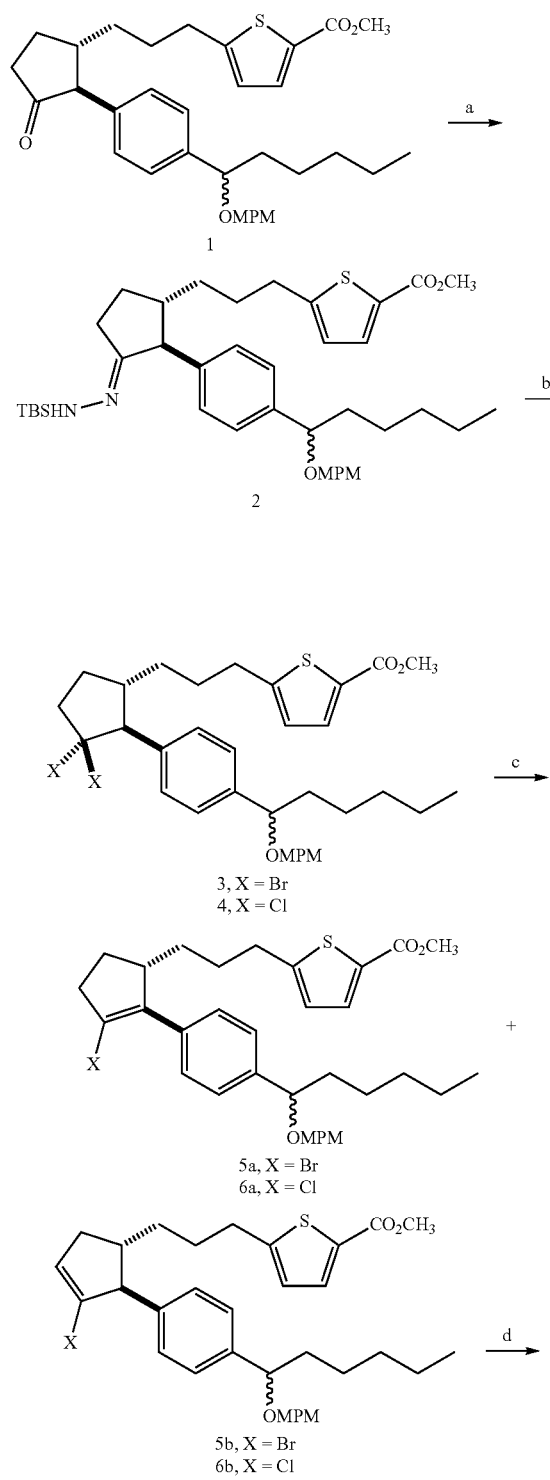

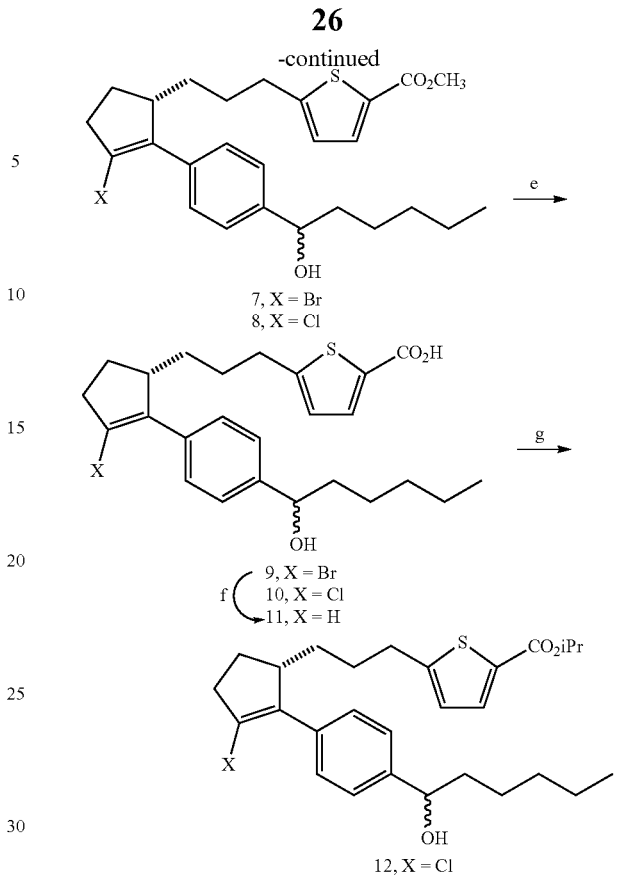

MPM = 4-methoxybenzyl

Conditions: (a) (TBSNH)₂, cat. Sc(OTf)₃, CHCl₃; (b) CuCl₂, Et₃N, MeOH; (c) 2-t-Butyl-1,1,3,3-tetramethylguanidine, ClCH₂CH₂Cl, rt or 60° C.; (d) DDQ, CH₂Cl₂/H₂O; (e) 1M LiOH, THF 60° C.; (f) tert-BuLi; MeOH; (g) DBU, 2-iodopropane, acetone.

TBS hydrazone of 5-[3-((1S,2s)-2-{4-[1-(4-Methoxy-benzyloxy)-hexyl]-phenyl}-3-oxo-cyclopentyl)-propyl]thiophene-2-carboxylic acid methyl ester (2)

The procedure of Furrows, M. E.; Myers, A. G. *J. Am. Chem. Soc.* 2004, 126, 5436 was followed: A solution of Sc(OTf)₃ (170 µL, 0.0017 mmol, 0.01 M/CH₃CN) was evaporated. A solution of ketone 1 (U.S. Provisional Patent Application No. 60/746,386 filed on May 4, 2006, 93 mg, 0.165 mmol) in 1 mL CHCl₃ was added by cannula, rinsing with 1 mL CHCl₃. The reaction was cooled in an ice bath and a solution of (TBSNH)₂ in 0.5 mL CHCl₃ was added, rinsing with 0.5 mL CHCl₃. After 30 min. at 0° C., the reaction was allowed to warm to room temperature (rt) overnight. The volatiles were evaporated under N₂ stream then at 1 mbar (30 min. at room temperature and 30 min. at 35° C.). The crude hydrazone was used directly in subsequent reactions.

5-[3-((1S,2S)-3,3-Dibromo-2-{4-[1-(4-methoxybenzyloxy)-hexyl]phenyl}-cyclopentyl)-propyl]-thiophene-2-carboxylic acid methyl ester (3)

A solution of Hydrazone 2 (prepared from 0.21 mmol of ketone as described above) in 1 mL CHCl₃ was cannula transferred to a mixture of CuBr₂ (325 mg, 1.46 mmol) and Et₃N (90 µL, 0.65 mmol) in MeOH (2.2 mL), rinsing with 1 mL CHCl₃. After 1 h, a solution of 10% conc. NH₄OH/saturated NH₄Cl was added and the mixture was extracted with CH₂Cl₂ (3×25 mL). The combined CH₂Cl₂ solution was dried (Na₂SO₄), filtered and evaporated. Purification by flash chromatography (20% ethyl acetate/hexanes) gave the title compound (52 mg, 35%).

5-[3-((1S,2S)-3,3-Dichloro-2-{4-[1-(4-methoxy-benzyloxy)-hexyl]-phenyl}-cyclopentyl)-propyl] thiophene-2-carboxylic acid methyl ester (4)

A solution of Hydrazone 2 (prepared from 0.11 mmol of ketone as described above) in 1 mL CHCl₃ was cannula transferred to a mixture of CuCl₂ (107 mg, 0.80 mmol) and Et₃N (50 µL, 0.36 mmol) in MeOH (1.2 mL), rinsing with 1 mL CHCl₃. After 1 h, a solution of 10% conc. NH₄OH/saturated NH₄Cl (8 mL) was added and the mixture was extracted with CH₂Cl₂ (3×30 mL). The combined CH₂Cl₂ solution was dried (Na₂SO₄), filtered and evaporated. Purification by flash chromatography (0%→20% ethyl acetate/hexanes) gave the title compound (34 mg, 49%).

5-[3-((S)-3-Bromo-2-{4-[1-(4-methoxy-benzyloxy)-hexyl]phenyl}-cyclopent-2-enyl)-propyl]thiophene-2-carboxylic acid methyl ester (5a)

A solution of dibromide 3 (52 mg, 0.074 mmol) and 2-tert-butyl-1,1,3,3-tetramethylguanidine (BTMG, 0.8 mL) in 1,2-dichloroethane (2 mL) was stirred at room temperature. After 3 days, 1 M HCl was added and the mixture was extracted with CH₂Cl₂ (3×25 mL). The combined dichloromethane solution was dried (Na₂SO₄), filtered and evaporated. Purification by flash chromatography (0%→20% ethyl acetate/hexanes) gave the title compound contaminated with 15% of the alkene regioisomer 5b as an inseparable mixture (45 mg, 97%).

5-[3-((S)-3-Chloro-2-{4-[1-(4-methoxy-benzyloxy)-hexyl]-phenyl}-cyclopent-2-enyl)-propyl]-thiophene-2-carboxylic acid methyl ester (6a)

A solution of dichloride 4 (12 mg, 0.019 mmol) and 2-tert-butyl-1,1,3,3-tetramethylguanidine (BTMG, 0.2 mL) in 1,2-dichloroethane (0.5 mL) was stirred at 60° C. After 70 h, 1 M HCl (28 mL) was added and the mixture was extracted with 20 mL CH₂Cl₂. The dichloromethane solution was washed further with 1 M HCl (3×25 mL) and then was dried (Na₂SO₄), filtered and evaporated. Purification by flash chromatography (0%→15% ethyl acetate/hexanes) gave the title compound, contaminated with 15% of the alkene regioisomer 6b as an inseparable mixture (10 mg, 93%).

5-(3-{(S)-3-Bromo-2-[4-(1-hydroxy-hexyl)-phenyl]-cyclopent-2-enyl}-propyl)-thiophene-2-carboxylic acid methyl ester (7) and 5-(3-{(S)-3-Chloro-2-[4-(1-hydroxy-hexyl)-phenyl]-cyclopent-2-enyl}-propyl)-thiophene-2-carboxylic acid methyl ester (8)

The previously described DDQ procedure was used (U.S. Pat. No. 7,091,231), which gave the title compounds, contaminated with 15% of the alkene regioisomer as inseparable mixtures.

5-(3-{(S)-3-Bromo-2-[4-(1-hydroxy-hexyl)-phenyl]-cyclopent-2-enyl}-propyl)-thiophene-2-carboxylic acid (9) and 5-(3-{(S)-3-Chloro-2-[4-(1-hydroxy-hexyl)-phenyl]-cyclopent-2-enyl}-propyl)-thiophene-2-carboxylic acid (10)

The previously described LiOH procedure was used at 60° C. overnight (U.S. Pat. No. 7,091,231), which gave the title compounds, contaminated with 15% of the alkene regioisomer as inseparable mixtures.

5-(3-{(S)-2-[4-(1-Hydroxy-hexyl)-phenyl]-cyclopent-2-enyl}-propyl)-thiophene-2-carboxylic acid (11)

A −78° C. solution of 9 (10 mg, 0.02 mmol) in THF (0.4 mL) was treated with tert-BuLi (60 µL, 0.01 mmol, 1.7 M/pentane). After 30 min., 2 mL saturated NH₄Cl solution was added and the resulting mixture was extracted with dichloromethane (3×20 mL). The combined dichloromethane solution was dried (Na₂SO₄), filtered and evaporated. The crude product still contained vinyl bromide 9 and so was resubmitted to the reaction conditions: THF (0.2 mL) and tert-BuLi (100 mL,) were added and the reaction was stirred for 3 h at −40° C. and then worked up as above. Purification by flash chromatography on silica gel (0%→30% MeOH/CH₂Cl₂) gave the title compound (4 mg, 0.01 mmol, 50%).

5-(3-{(S)-3-Chloro-2-[4-(1-hydroxy-hexyl)-phenyl]-cyclopent-2-enyl}-propyl)-thiophene-2-carboxylic acid isopropyl ester (12)

The previously described DBU/2-iodopropane procedure was used (U.S. Pat. No. 7,091,231), which gave the title compound contaminated with 15% of the other alkene regioisomer as an inseparable mixture.

Scheme 2

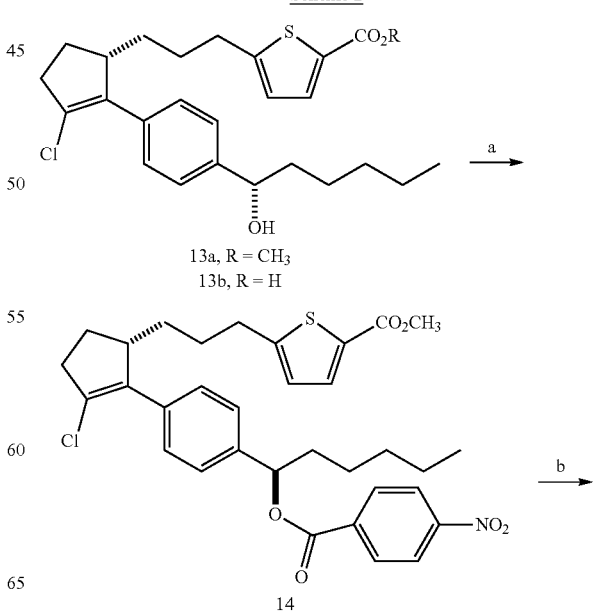

13a, R = CH₃
13b, R = H

14

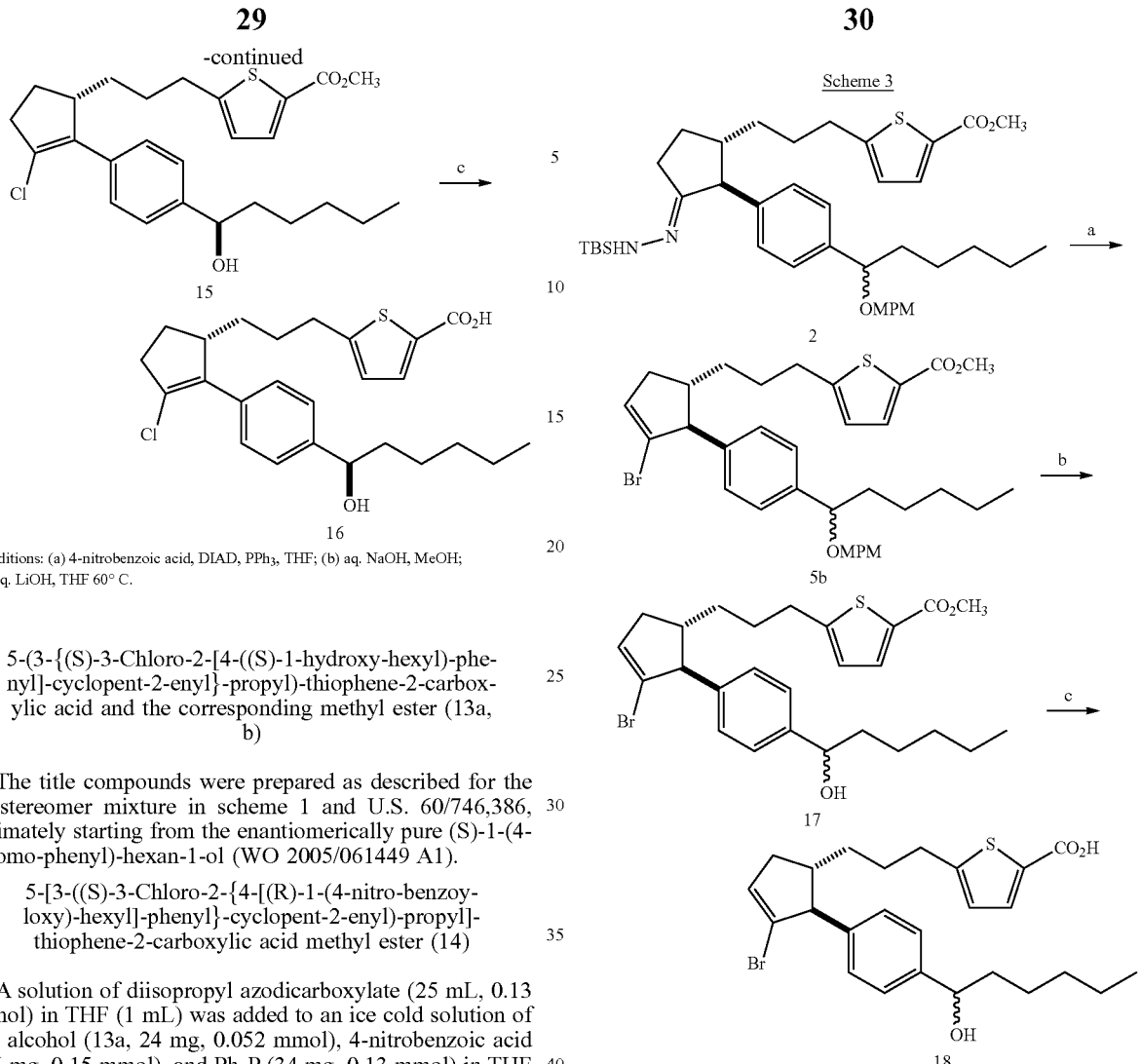

Conditions: (a) 4-nitrobenzoic acid, DIAD, PPh₃, THF; (b) aq. NaOH, MeOH; (c) aq. LiOH, THF 60° C.

5-(3-{(S)-3-Chloro-2-[4-((S)-1-hydroxy-hexyl)-phenyl]-cyclopent-2-enyl}-propyl)-thiophene-2-carboxylic acid and the corresponding methyl ester (13a, b)

The title compounds were prepared as described for the diastereomer mixture in scheme 1 and U.S. 60/746,386, ultimately starting from the enantiomerically pure (S)-1-(4-Bromo-phenyl)-hexan-1-ol (WO 2005/061449 A1).

5-[3-((S)-3-Chloro-2-{4-[(R)-1-(4-nitro-benzoyloxy)-hexyl]-phenyl}-cyclopent-2-enyl)-propyl]-thiophene-2-carboxylic acid methyl ester (14)

A solution of diisopropyl azodicarboxylate (25 mL, 0.13 mmol) in THF (1 mL) was added to an ice cold solution of the alcohol (13a, 24 mg, 0.052 mmol), 4-nitrobenzoic acid (26 mg, 0.15 mmol), and Ph₃P (34 mg, 0.13 mmol) in THF (1 mL). The solution was allowed to warm to room temperature and after 1.5 h, saturated NaHCO₃ solution (15 mL) was added. The resulting mixture was extracted with ethyl acetate (2×20 mL) and the combined ethyl acetate solution was dried (MgSO₄), filtered and evaporated. Purification by flash chromatography on silica gel (0%→40% ethyl acetate/hexanes) gave the title compound (18 mg, 0.03 mmol, 57%).

5-(3-{(S)-3-Chloro-2-[4-((R)-1-hydroxy-hexyl)-phenyl]-cyclopent-2-enyl}-propyl)-thiophene-2-carboxylic acid methyl ester (15)

A solution of 5% NaOH/MeOH (0.25 mL, 0.31 mmol), ester 14 (18 mg, 0.029 mmol) and THF (0.05 mL) was allowed to stir at room temperature. After 30 min., 10 mL 1 M HCl solution was added and the resulting mixture was extracted with ethyl acetate (2×20 mL). The combined ethyl acetate solution was dried (MgSO₄), filtered and evaporated. Purification by flash chromatography on silica gel (0%→50% ethyl acetate/hexanes) gave the title compound (11 mg, 0.024 mmol, 82%).

5-(3-{(S)-3-Chloro-2-[4-((R)-1-hydroxy-hexyl)-phenyl]-cyclopent-2-enyl}-propyl)-thiophene-2-carboxylic acid (16)

The previously described LiOH procedure (U.S. Pat. No. 7,091,231) was used at 60° C. overnight.

Conditions: (a) Br₂, 2-t-Butyl-1,1,3,3-tetramethylguanidine, CH₂Cl₂ -78° C.; (b) DDQ, CH₂Cl₂/H₂O; (c) 1M LiOH, THF 60° C.

5-[3-((1S,2S)-3-Bromo-2-{4-[1-(4-methoxy-benzyloxy)-hexyl]-phenyl}-cyclopent-3-enyl)-propyl]thiophene-2-carboxylic acid methyl ester (5b, scheme 3)

Br₂ (70 µL, 1.36 mmol) was added dropwise to a −78° C. solution of BTMG (600 µL) in dichloromethane (1.8 mL). The resulting colorless solution was warmed to room temperature and was stirred for 15 min. A solution of hydrazone 2 (prepared from 0.17 mmol of ketone 1) in dichloromethane (1 mL) was added, rinsing with 1 mL dichloromethane. After 1 h at room temperature, the reaction was cooled to 0° C. and more Br₂ (70 µL, 1.36 mmol) was added. The reaction was allowed to warm to room temperature, was stirred overnight and then was quenched by addition of saturated NH₄Cl solution. The resulting mixture was extracted with dichloromethane (3×20 mL) and the combined dichloromethane solution was washed with brine and then was dried (Na₂SO₄), filtered and evaporated. Purification by flash chromatography on silica gel (0%→50% ethyl acetate/hexanes) provided the title compound (51 mg, 50%).

5-(3-{(1S,2S)-3-Bromo-2-[4-(1-hydroxy-hexyl)-phenyl]-cyclopent-3-enyl}-propyl)-thiophene-2-carboxylic acid methyl ester (17)

The previously described DDQ procedure was used (U.S. Pat. No. 7,091,231).

5-(3-{(1S,2S)-3-Bromo-2-[4-(1-hydroxy-hexyl)-phenyl]-cyclopent-3-enyl}-propyl)-thiophene-2-carboxylic acid (18)

The previously described LiOH procedure was used at 60° C. overnight (U.S. Pat. No. 7,091,231).

Scheme 4

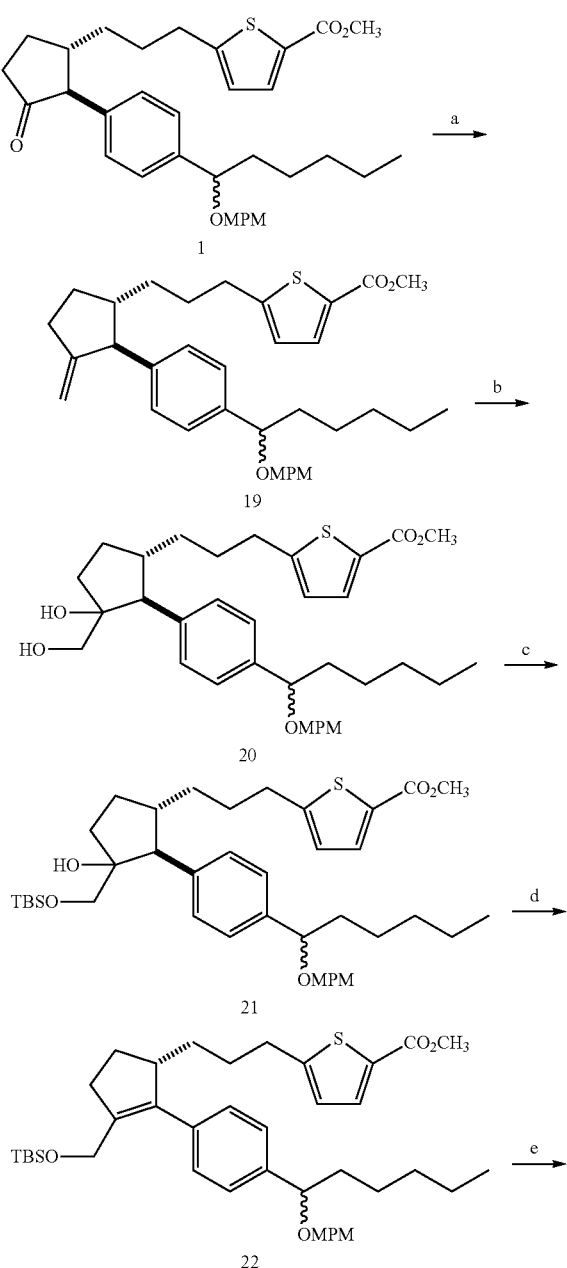

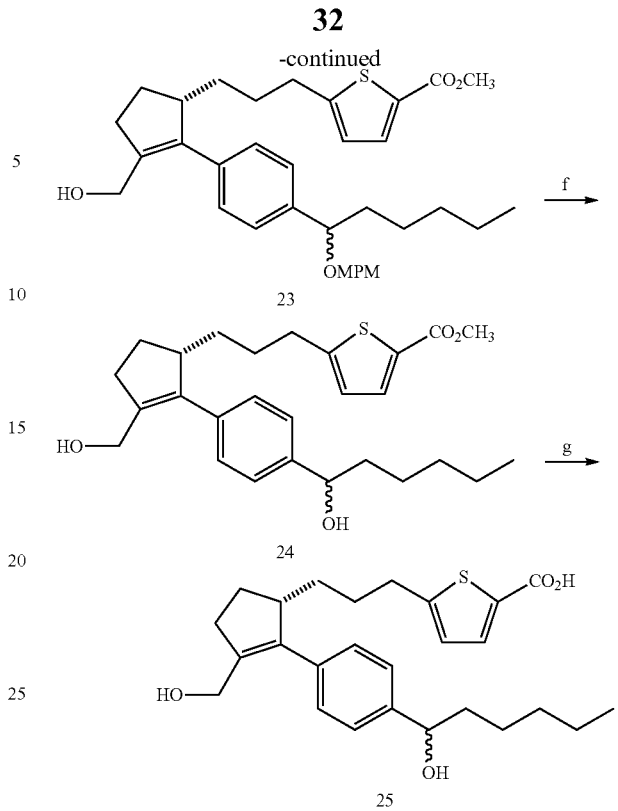

Conditions: (a) Tebbe reagent, toluene; (b) $OsO_4$, NMO, acetone; (c) TBSOTf, 2,6-lutidine, $ClCH_2CH_2Cl$; (d) Methyl N-(triethylammoniumsulphonyl)carbamate (Burgess reagent), PhH 50° C.; (e) HF·pyridine, $CH_3CN$ 0° C.; (f) DDQ, $H_2O/CH_2Cl_2$; (g) 1M LiOH, THF 60° C.

5-[3-((1S,2R)-2-{4-[1-(4-Methoxy-benzyloxy)-hexyl]-phenyl}-3-methylene-cyclopentyl)-propyl]-thiophene-2-carboxylic acid methyl ester (19)

A solution of ketone 1 (143 mg, 0.25 mmol) in toluene (1.2 mL) was cannula transferred to an ice-cold solution of the Tebbe reagent-bis(cyclopentadienyl)-µ-chloro(dimethylaluminum)-µ-methylenetitanium (1.6 mL, 0.80 mmol, 0.5 M/toluene) in 1.2 mL toluene, rinsing with 1.2 mL toluene. The reaction was allowed to warm to room temperature and after 1 h was quenched by addition of 0.2 mL 6 M NaOH (0° C.). The resulting mixture was warmed to room temperature, diluted with 40 mL of dichloromethane, and then was dried ($Na_2SO_4$), filtered and evaporated. Purification by flash chromatography (0% ethyl acetate/hexanes→100%) gave the title compound (97 mg, 86%).

5-[3-((1S,2S)-3-Hydroxy-3-hydroxymethyl-2-{4-[1-(4-methoxy-benzyloxy)-hexyl]-phenyl}-cyclopentyl)-propyl]-thiophene-2-carboxylic acid methyl ester (20)

An aqueous solution of $OsO_4$ (0.32 mL, 0.05 mmol, 4 wt. %) was added to an ice-cold mixture of alkene 19 (59 mg, 0.10 mmol) and NMO (4-methylmorpholine N-oxide, 27 mg, 0.23 mmol) in acetone (2.2 mL). The reaction was allowed to warm to room temperature and after 1 h, 5 mL saturated $NaHCO_3$ was added. The resulting mixture was extracted with ethyl acetate (3×30 mL), washed with brine and then was dried ($Na_2SO_4$), filtered and evaporated.

Purification by flash chromatography on silica gel (0%→100% ethyl acetate/hexanes) gave the title compound (51 mg, 82%).

5-[3-((1S,2S)-3-(tert-Butyl-dimethyl-silanyloxymethyl)-3-hydroxy-2-{4-[1-(4-methoxy-benzyloxy)-hexyl]-phenyl}-cyclopentyl)-propyl]-thiophene-2-carboxylic acid methyl ester (21)

TBSOTf (16 µL, 0.070 mmol) was added to a 0° C. solution of alcohol 20 (37 mg, 0.063 mmol) and 2,6-lutidine (16 µL, 0.14 mmol) in ClCH$_2$CH$_2$Cl (0.5 mL). The reaction was allowed to warm to room temperature and after 2 h, saturated NaHCO$_3$ solution was added. The resulting mixture was extracted with dichloromethane (3×20 mL) and the combined dichloromethane solution was washed with brine and then was dried (Na$_2$SO$_4$), filtered and evaporated. Purification by flash chromatography on silica gel (ethyl acetate/hexanes) provided the title compound (39 mg, 87%).

5-[3-((S)-3-(tert-Butyl-dimethyl-silanyloxymethyl)-2-{4-[1-(4-methoxy-benzyloxy)-hexyl]-phenyl}-cyclopent-2-enyl)-propyl]thiophene-2-carboxylic acid methyl ester (22)

A solution of 21 (46 mg, 0.065 mmol) and methyl N-(triethylammoniumsulphonyl)carbamate (Burgess reagent, 62 mg, 0.26 mmol) in benzene (0.9 mL) was heated at 50° C. After 1 h, the reaction was quenched by addition of H$_2$O and the resulting mixture was extracted with dichloromethane (3×20 mL). The combined organic solution was washed with brine and then was dried (Na$_2$SO$_4$), filtered and evaporated. Purification by flash chromatography on silica gel (ethyl acetate/hexanes) gave the title compound (31 mg, 68%).

5-[3-((S)-3-Hydroxymethyl-2-{4-[1-(4-methoxy-benzyloxy)-hexyl]-phenyl}-cyclopent-2-enyl)-propyl]-thiophene-2-carboxylic acid methyl ester (23)

The previously described HF.pyridine procedure was used (U.S. Pat. No. 7,091,231).

5-(3-{(S)-2-[4-(1-Hydroxy-hexyl)-phenyl]-3-hydroxymethyl-cyclopent-2-enyl}-propyl)-thiophene-2-carboxylic acid methyl ester (24)

The previously described DDQ procedure was used (U.S. Pat. No. 7,091,231).

5-(3-{(S)-2-[4-(1-Hydroxy-hexyl)-phenyl]-3-hydroxymethyl-cyclopent-2-enyl}-propyl)-thiophene-2-carboxylic acid (25)

The previously described LiOH procedure was used at 60° C. overnight (U.S. Pat. No. 7,091,231).

Scheme 5

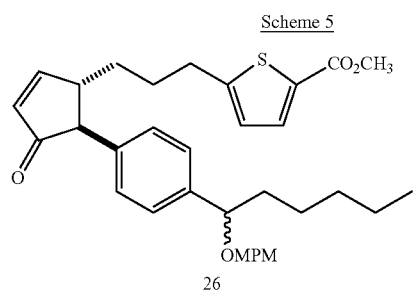

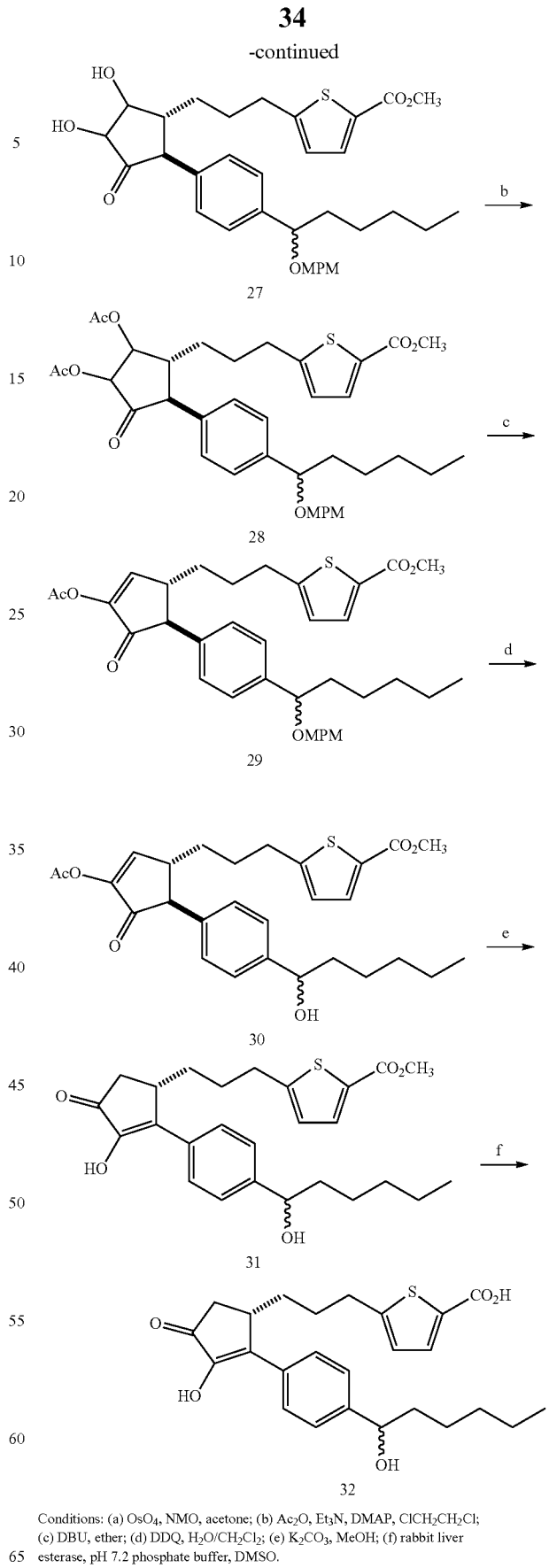

Conditions: (a) OsO$_4$, NMO, acetone; (b) Ac$_2$O, Et$_3$N, DMAP, ClCH$_2$CH$_2$Cl; (c) DBU, ether; (d) DDQ, H$_2$O/CH$_2$Cl$_2$; (e) K$_2$CO$_3$, MeOH; (f) rabbit liver esterase, pH 7.2 phosphate buffer, DMSO.

5-[3-((1R,5S)-2,3-Dihydroxy-5-{4-[1-(4-methoxy-benzyloxy)-hexyl]-phenyl}-4-oxo-cyclopentyl)-propyl]thiophene-2-carboxylic acid methyl ester (27)

A solution of OsO₄ (220 µL, 0.036 mmol, 4 wt %/H₂O) was added dropwise to a 0° C. mixture of 5-[3-((1 S,5 S)-5-{4-[1-(4-Methoxy-benzyloxy)-hexyl]-phenyl}-4-oxo-cyclopent-2-enyl)-propyl]-thiophene-2-carboxylic acid methyl ester (26) (39 mg, 0.070 mmol, see U.S. 60/746,386) and NMO (16 mg, 0.14 mmol). The reaction was allowed to warm to room temperature and after 1 h, was quenched by addition of 5% NaHSO₃ solution. The resulting mixture was extracted with ethyl acetate (3×30 mL) and the combined ethyl acetate solution was washed with brine and then was dried (Na₂SO₄), filtered and evaporated. Purification by flash chromatography on silica gel (ethyl acetae/hexanes) provided the title compound (15 mg, 36%).

5-[3-((1R,5S)-2,3-Diacetoxy-5-{4-[1-(4-methoxy-benzyloxy)-hexyl]-phenyl}-4-oxo-cyclopentyl)-propyl]-thiophene-2-carboxylic acid methyl ester (28)

Ac₂O (100 µL, 1.06 mmol), Et₃N (160 µL, 1.15 mmol) and DMAP (26 mg, 0.21 mmol) were added to a solution of the diol (27, 55 mg, 0.093 mmol) in ClCH₂CH₂Cl (0.5 mL). The reaction was stirred overnight, diluted with ethyl acetate and then washed with 1 M HCl, saturated NaHCO₃, and brine. The ethyl acetate solution was then dried (Na₂SO₄), filtered and evaporated. Purification by flash chromatography on silica gel (ethyl acetate/hexanes) provided the title compound (32 mg, 51%).

5-[3-((1S,5S)-3-Acetoxy-5-{4-[1-(4-methoxy-benzyloxy)-hexyl]-phenyl}-4-oxo-cyclopent-2-enyl)-propyl]-thiophene-2-carboxylic acid methyl ester (29)

DBU (15 µL, 0.10 mmol) was added to an ice-cold solution of diacetate 28 (32 mg, 0.048 mmol) in ether (0.5 mL). The solution was stirred at 0° C. for 30 min. and then was allowed to warm to room temperature. After stirring overnight, 1 M HCl was added and the resulting mixture was extracted with ethyl acetate (3×25 mL). The combined organic solution was washed with brine and then was dried (Na₂SO₄), filtered and evaporated. Purification by flash chromatography on silica gel (0%→100% ethyl acetate/hexanes) provided the title compound (21 mg, 71%).

5-(3-{(1S,5S)-3-Acetoxy-5-[4-(1-hydroxy-hexyl)-phenyl]-4-oxo-cyclopent-2-enyl}-propyl)-thiophene-2-carboxylic acid methyl ester (30)

The previously described (U.S. Pat. No. 7,091,231) DDQ procedure was used.

5-(3-{(S)-3-Hydroxy-2-[4-(1-hydroxy-hexyl)-phenyl]-4-oxo-cyclopent-2-enyl}-propyl)-thiophene-2-carboxylic acid methyl ester (31)

K₂CO₃ (6 mg, 0.046 mmol) was added to a solution of 30 (12 mg, 0.019 mmol) in methanol (0.55 mL). After 2 h, excess saturated NH₄Cl solution was added and the resulting mixture was extracted with dichloromethane (3×20 mL). The combined organic solution was dried, filtered and evaporated. Purification by flash chromatography on silica gel (ethyl acetate/hexanes) provided the title compound (5 mg, 58%).

5-(3-{(S)-3-Hydroxy-2-[4-(1-hydroxy-hexyl)-phenyl]-4-oxo-cyclopent-2-enyl}-propyl)-thiophene-2-carboxylic acid (32)

A mixture of 31 (5 mg, 0.011 mmol), rabbit liver esterase (3 mg, Aldrich), DMSO (50 µL) and pH 7.2 phosphate buffer (0.5 mL) was stirred at room temperature overnight. The reaction was diluted with CH₂Cl₂ and washed with H₂O and brine. The resulting organic solution was dried (Na₂SO₄), filtered and evaporated. Purification by flash chromatography on silica gel (0%→30% methanol/dichloromethane) gave the title compound (1 mg, 21%).

Scheme 6

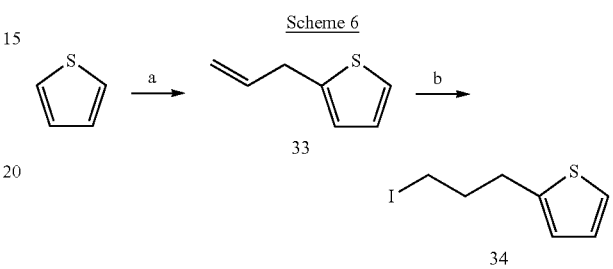

Conditions: (a) n-BuLi, ether; allyl bromide, CuCN; (b) Cp₂ZrHCl, THF; NIS.

2-Allylthiophene (33)

n-Butyllithium (21.5 mL, 34.4 mmol) was added to an ice cold solution of thiophene (2.5 mL, 31.2 mmol) in ether (60 mL). After 1.5 h, the mixture was cooled to −78° C. and allyl bromide (2.9 mL, 34.3 mmol) and CuCN (325 mg, 3.6 mmol) were added. The resulting mixture was stirred for 10 min. at 0° C. and then allowed to warm to room temperature. After 50 min., saturated NH₄Cl solution (100 mL) was added and the mixture was extracted with ether (2×100 mL). The combined ether solution was dried (Na₂SO₄), filtered and evaporated to give the title compound (3.668 g, 29.5 mmol, 95%).

2-(3-Iodo-propyl)-thiophene (34)

Cp₂ZrHCl (9.141 g, 35.4 mmol) was added to a solution of 33 (3.668 g, 29.5 mmol) in THF (50 mL). The mixture was stirred for 1.5 h at 40° C., cooled to 0° C. and was then treated with N-iodosuccinimide (NIS, 7.972 g, 35.4 mmol). The reaction was allowed to warm to room temperature and after 75 min., 100 mL of saturated NaHCO₃ solution was added. The mixture was extracted with ether (2×100 mL) and the combined ether solution was dried (Na₂SO₄), filtered and evaporated. The residue was purified on a Teledyne Isco Combiflash unit (330 g silica gel column, 0%→20% ethyl acetate/hexanes) which gave the title compound (4.558 g, 18.1 mmol, 61%).

Scheme 7

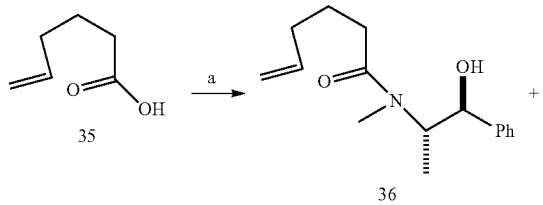

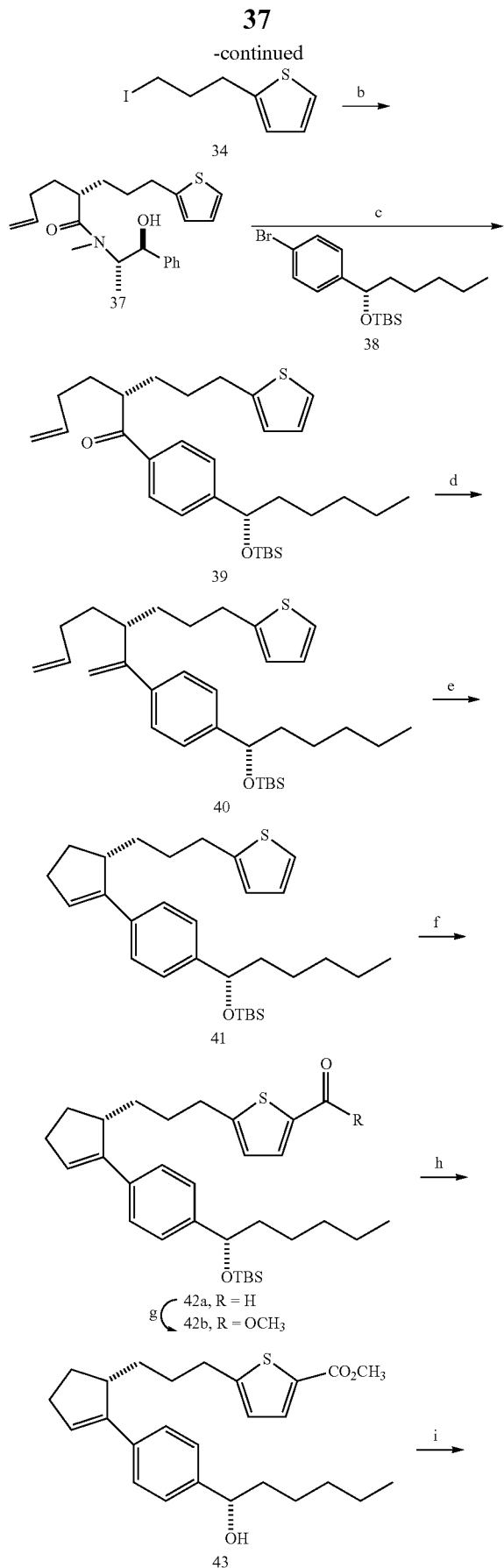

Conditions: (a) (COCl)₂, cat. DMF, CH₂Cl₂; (+)-pseudoephederine, TEA; (b) LDA, LiCl, THF; 1; (c) 1 eq. n-BuLi, THF; 2, tert-BuLi; (d) TMSCH₂Li, THF; KH, THF; (e) Grubbs II catalyst, toluene, 50° C.; (f) n-BuLi, ether 0° C.; DMF; (g) HOAc, NaCN, MnO₂, MeOH; (h) TBAF; (i) 1M LiOH, THF 60° C.

Hex-5-enoic acid ((1S,2S)-2-hydroxy-1-methyl-2-phenyl-ethyl)-methyl-amide (36)

A similar procedure to that described in Myers, A. G.; Yang, B. H.; Chen, H.; McKinstry, L.; Kopecky, D. J.; Gleason, J. L. *J. Am. Chem. Soc.* 1997, 119, 6496 was followed. (COCl)₂ and DMF were added to a solution of 6-hexenoic acid (35, 3.168 g, 27.7 mmol) in CH₂Cl₂ (14 mL). After 2 h, the solution was cannula transferred to an ice cold solution of (+)-pseudoephedrine (3.818 g, 23.1 mmol) and triethylamine (4.5 mL, 32.3 mmol) in 45 mL CH₂Cl₂. The resulting mixture was allowed to warm to room temperature and after 10 min., 5 mL water was added. The mixture was washed with brine (3×25 mL) and the CH₂Cl₂ layer was dried (MgSO₄), filtered and evaporated. The residue was purified on a Teledyne Isco Combiflash unit (330 g silica gel column, 20%→100% ethyl acetate/hexanes) which gave the title compound (4.795 g, 18.3 mmol, 79%).

(S)-2-(3-Thiophen-2-yl-propyl)-hex-5-enoic acid ((1S,2S)-2-hydroxy-1-methyl-2-phenyhethyl)-methyl-amide (37)

A similar procedure to that described in Myers, A. G.; Yang, B. H.; Chen, H.; McKinstry, L.; Kopecky, D. J.; Gleason, J. L. *J. Am. Chem. Soc.* 1997, 119, 6496 was followed. n-BuLi (5.7 mL, 14.3 mmol) was added to a −78° C. mixture of LiCl (1.965 g, 46.3 mmol, flame dried under vacuum) and i-Pr₂NH (2.1 mL, 14.9 mmol) in 10 mL THF. The mixture was stirred at 0° C. for 5 min. and was then recooled to −78° C. At this time, a solution of amide 34 (1.949 g, 7.5 mmol) in THF (18 mL) was added over 5 min. (cannula), rinsing with 5 mL THF. The resulting mixture was stirred for 1 h at −78° C., 15 min. at 0° C. and 5 min. at room temperature. The reaction was cooled to 0° C. and a solution of iodide 34 (1.271 g, 5.0 mmol) in 2 mL THF was added by cannula, rinsing with 1 mL THF. The reaction was stirred at 0° C. overnight and then was quenched by addition of 50 mL saturated NH₄Cl solution. The resulting mixture was extracted with ethyl acetate (3×50 mL) and the combined ethyl acetate solution was dried (MgSO₄), filtered and evaporated. The residue was purified by flash chromatography on a Combiflash unit by Teledyne Isco (330 g silica gel, 10%→85% ethyl acetate/hexanes) which gave the title compound (1.793 g, 5.0 mmol, 100%).

(S)-1-{4-[(S)-1-(tert-Butyl-dimethyl-silanyloxy)-hexyl]-phenyl}-2-(3-thiophen-2-yl-propyl)-hex-5-en-1-one (39)

Tert-BuLi (0.3 mL, 0.51 mmol, 1.7 M/pentane) was added to a −78° C. solution of aryl bromide 38 (86 mg, 0.25 mmol, U.S. Prov PA 60/894,267) in 0.5 mL THF. The solution was stirred for 40 min. and was then used as described below.

In another flask, n-BuLi (0.11 mL, 0.18 mmol) was added to a −78° C. solution of amide 37 (65 mg, 0.17 mmol) in 0.5 mL THF. After 20 min., the aryllithium solution prepared above was added by cannula. The reaction was allowed to warm to 0° C. and after 30 min., i-Pr₂NH (24 μL, 0.17 mmol) was added followed by 10 mL 10% HOAc/ether. The resulting mixture was stirred for 1 h and then 10 mL saturated NaHCO₃ solution was added. The resulting mixture was extracted with ethyl acetate (2×20 mL) and the combined solution was dried (Na₂SO₄), filtered and evaporated. The residue was purified by flash chromatography using a Combiflash unit by Teledyne Isco (12 g silica gel, 0%→20% ethyl acetate/hexanes) which gave the title compound (47 mg, 0.092 mmol, 54%).

tert-Butyl-dimethyl-((S)-1-{4-[(S)-1-methylene-2-(3-thiophen-2-yl-propyl)-hex-5-enyl]-phenyl}-hexyloxy)-silane (40)

TMSCH₂Li (1.2 mL, 1.2 mmol, 1 M/THF) was added to a −78° C. solution of ketone 39 (645 mg, 1.26 mmol) in 5 mL THF. The reaction was stirred at 0° C. for 1.5 h and then 50 mL saturated NH₄Cl solution was added. The resulting mixture was extracted with ethyl acetate (2×50 mL) and the combined ethyl acetate solution was dried (Na₂SO₄), filtered and evaporated.

The crude teriary alcohol was co-evaporated with benzene, taken into 2.5 mL THF and the solution cannula transferred to a mixture of KH (505 mg, 3.8 mmol, 30% in oil) in 2.5 mL THF. After 50 min., the reaction was cooled in an ice bath and 50 mL saturated NH₄Cl solution was added. The mixture was extracted with ethyl acetate (2×50 mL) and the combined ethyl acetate solution was dried (Na₂SO₄), filtered and evaporated. Purification by flash chromatography on a Combiflash unit by Teledyne Isco (120 g silica gel silica gel, 0%→15% ethyl acetate/hexanes) gave the title compound (199 mg, 0.39 mmol, 31%) along with 271 mg of mixed fractions.

tert-Butyl-dimethyl-((S)-1-{4-[(S)-5-(3-thiophen-2-yl-propyl)-cyclopent-1-enyl]-phenyl}-hexyloxy)-silane (41)

A toluene (39 mL) solution of diene 40 (199 mg, 0.39 mmol) and Grubbs $2^{nd}$ generation catalyst (33 mg, 0.04 mmol, Aldrich) was stirred at 50° C. for 3 h. The reaction was stored in the freezer overnight and then was evaporated and purified by flash chromatography using a Combiflash unit by Teledyne Isco (80 g silica gel, 0%→10% ethyl acetate/hexanes) to give the title compound (177 mg, 0.37 mmol, 94%).

5-[3-((S)-2-{4-[(S)-1-(tert-Butyl-dimethyl-silanyloxy)-hexyl]-phenyl}-cyclopent-2-enyl)-propyl]thiophene-2-carbaldehyde (42a)

n-Butyllithium (0.14 mL, 0.22 mmol, 1.6 M/hexanes) was added to an ice cold solution of 41 (53 mg, 0.11 mmol) in 0.5 mL ether. After 1 h, DMF (85 μL, 1.1 mmol) was added and the reaction was allowed to stir for 40 min. At this time, the reacton was quenched by addition of 10 mL saturated NH₄Cl solution. The mixture was extracted with ethyl acetate (2×20 mL) and the combined ethyl acetate solution was dried (Na₂SO₄), filtered and evaporated. The residue was purified by flash chromatography using a Combiflash unit by Teledyne Isco (12 g silica gel, 0%→15% ethyl acetate/hexanes) which gave the title compound (43 mg, 0.084 mmol, 77%).

5-[3-((S)-2-{4-[(S)-1-(tert-Butyl-dimethyl-silanyloxy)-hexyl]-phenyl}-cyclopent-2-enyl)-propyl]-thiophene-2-carboxylic acid methyl ester (42b)

Acetic acid (12 μL, 0.21 mmol), NaCN (25 mg, 0.51 mmol) and MnO₂ (152 mg, 1.7 mmol) were added to a mixture of 42a (43 mg, 0.084 mmol) in methanol (0.5 mL). The mixture was stirred for 18 h and then was filtered through Celite, washing with ethyl acetate. The filtrate was washed with water (20 mL) and the aqueous layer was further extracted with ethyl acetate (20 mL). The combined ethyl acetate solution was dried (Na₂SO₄), filtered and evaporated to give the title compound (45 mg, 0.083 mmol, 99%).

5-(3-{(S)-2-[4-((S)-1-Hydroxy-hexyl)-phenyl]-cyclopent-2-enyl}-propyl)-thiophene-2-carboxylic acid methyl ester (43)

TBAF (0.4 mL, 0.4 mmol, 1 M/THF) was added to 42b (45 mg, 0.083 mmol) and the resulting solution was allowed to stir for 4 h. Saturated NH₄Cl (20 mL) solution was added and the mixture was extracted with ethyl acetate (2×20 mL). The combined ethyl acetate solution was dried (Na₂SO₄), filtered and evaporated. Purification of the residue by flash chromatography using a Combiflash unit by Teledyne Isco (330 g silica gel, 0%→20% ethyl acetate/hexanes) gave the title compound (26 mg, 0.061 mmol, 73%).

5-(3-{(S)-2-[4-((S)-1-Hydroxy-hexyl)-phenyl]-cyclopent-2-enyl}-propyl)-thiophene-2-carboxylic acid (44)

LiOH (0.5 mL, 0.5 mmol, 1 M) was added to a THF (1.5 mL) solution of 43 (14 mg, 0.033 mmol). The mixture was stirred overnight at 60° C., allowed to cool to room temperature and then quenched by addition of 1 M HCl (10 mL). The mixture was extracted with CH₂Cl₂ (3×15 mL) and the combined CH₂Cl₂ solution was dried (Na₂SO₄), filtered and evaporated to leave the title compound (13 mg, 0.031 mmol, 95%).

Scheme 8

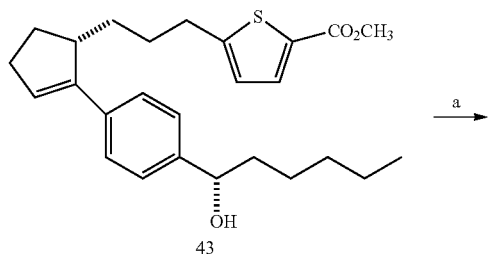

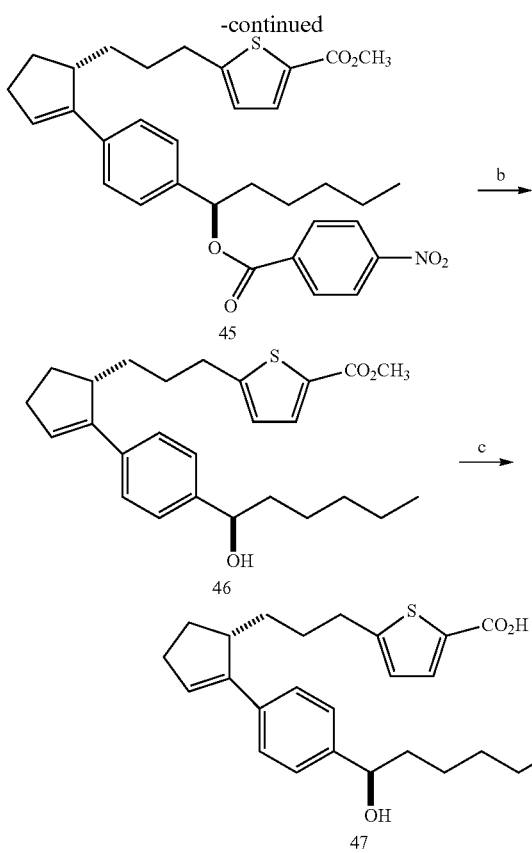

Conditions: (a) DIAD, 4-nitrobenzoic acid, Ph₃P, THF;
(b) K₂CO₃, MeOH; (c) 1M LiOH, THF 60° C.

5-[3-((S)-2-{4-[(R)-1-(4-Nitro-benzoyloxy)-hexyl]-phenyl}-cyclopent-2-enyl)-propyl]-thiophene-2-carboxylic acid methyl ester (45)

Diisopropyl azodicarboxylate (DIAD, 53 µL, 0.27 mmol) in 1 mL THF was cannula transferred to an ice cold solution of 43 (46 mg, 0.11 mmol), Ph₃P (66 mg, 0.25 mmol) and 4-nitrobenzoic acid (50 mg, 0.30 mmol). The solution was allowed to warm to room temperature and after 2.5 h, 20 mL saturated NaHCO₃ solution was added. The resulting mixture was extracted with ethyl acetate (2×25 mL) and the combined solution was dried (Na₂SO₄), filtered and evaporated. The residue was purified by flash chromatography using a Combiflash unit by Teledyne Isco (12 g silica gel, 0%→15% ethyl acetate/hexanes) to give the title compound (40 mg, 0.069 mmol, 63%).

5-(3-{(S)-2-[4-((R)-1-Hydroxy-hexyl)-phenyl]-cyclopent-2-enyl}-propyl)-thiophene-2-carboxylic acid methyl ester (46)

A mixture of 45 (40 mg, 0.069 mmol), K₂CO₃ (10 mg, 0.072 mmol) in methanol (0.5 mL) was stirred at room temperature. After 1 h, the diester had not dissolved and so 0.2 mL THF was added. The reaction was stirred further for 1.5 h and then 10 mL 1 M HCl was added. The mixture was extracted with ethyl acetate (2×20 mL) and the combined solution was dried (Na₂SO₄), filtered and evaporated. Purification of the residue by flash chromatography using a Combiflash unit by Teledyne Isco (12 g silica gel, 0%→20% ethyl acetate/hexanes) gave the title compound (22 mg, 0.051 mmol, 75%).

5-(3-{(S)-2-[4-((R)-1-Hydroxy-hexyl)-phenyl]-cyclopent-2-enyl}-propyl)-thiophene-2-carboxylic acid (47)

The procedure described above for the S diastereomer was used.

Scheme 9

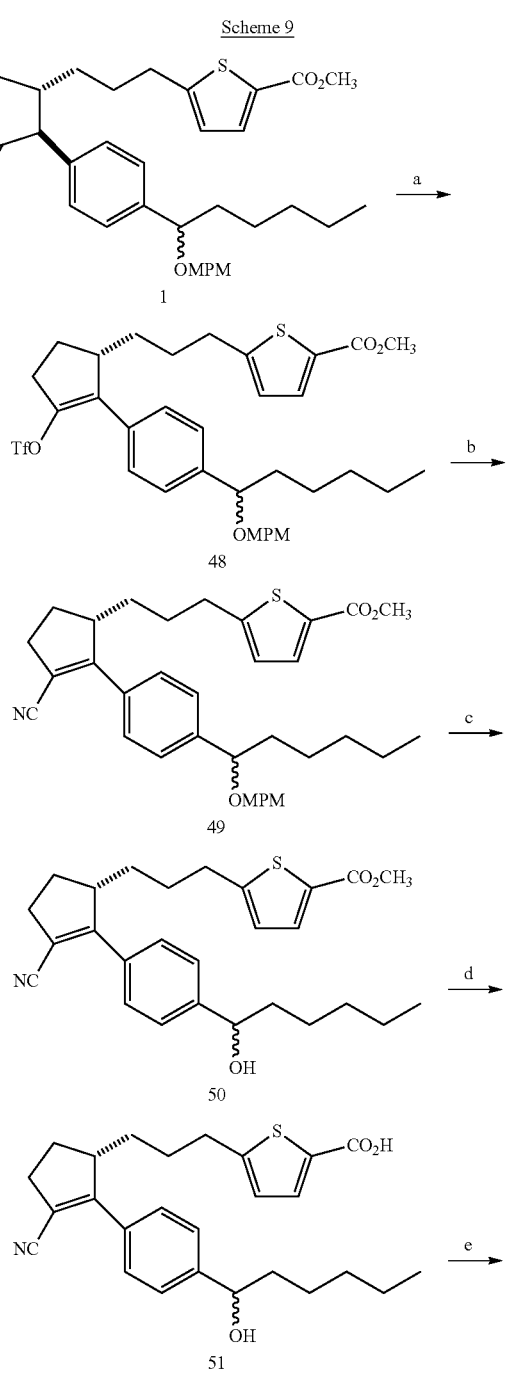

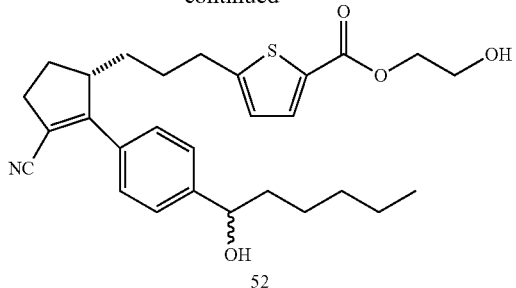

52

Conditions: (a) NaH, DMF; PhNTf$_2$; (b) NaCN, CuI, Pd(Ph$_3$P)$_4$, CH$_3$CN 90° C.; (c) DDQ, CH$_2$Cl$_2$/H$_2$O; (d) 1M LiOH, THF 60° C.; (e) ClCO$_2$Et, Et$_3$N; HOCH$_2$CH$_2$OH.

5-[3-((S)-2-{4-[1-(4-Methoxy-benzyloxy)-hexyl]-phenyl}-3-trifluoromethanesulfonyloxy-cyclopent-2-enyl)-propyl]-thiophene-2-carboxylic acid methyl ester (48)

A solution of ketone 1 (1.0401 g, 1.85 mmol) in 4.6 mL DMF was cannula transferred to an ice cold mixture of NaH (255 mg, 6.38 mmol, 60%/oil) in 4.6 mL DMF. After 3 h, a solution of PhNTf$_2$ (875 mg, 2.45 mmol) in 5 mL DMF was added and the reaction mixture was allowed to warm to room temperature. After overnight stirring, the reaction was quenched by addition of 10 mL saturated NaHCO$_3$ solution. Water, 50 mL, and 30 mL saturated NH$_4$Cl solution were added and the resulting mixture was extracted with ethyl acetate (3×30 mL). The combined ethyl acetate solution was washed with water (3×50 mL) and brine (50 mL) and then was dried (Na$_2$SO$_4$), filtered and evaporated. The residue was purified by flash chromatography using a Combiflash unit by Teledyne Isco (120 g silica gel, 0%→100% ethyl acetate/hexanes) to give the title compound (174 mg, 14%) along with the corresponding free acid (569 mg, 45%).

5-[3-((S)-3-Cyano-2-{4-[1-(4-methoxy-benzyloxy)-hexyl]-phenyl}-cyclopent-2-enyl)-propyl]-thiophene-2-carboxylic acid methyl ester (49)

A solution of vinyl triflate 48 (61 mg, 0.088 mmol) in 1 mL CH$_3$CN was cannula transferred to a flask containing NaCN (21 mg, 0.42 mmol, dried under vacuum at 105° C. over 3 days), CuI (13 mg, 0.069 mmol), and (Ph$_3$P)$_4$Pd (8 mg, 0.0066 mmol), rinsing with 1 mL CH$_3$CN. The reaction was stirred at 90° C. for 2 h, cooled to room temperature and then filtered through Celite, washing with ethyl acetate. The filtrate was washed with 20 mL water and 20 mL brine and then was dried (Na$_2$SO$_4$), filtered and evaporated. The residue was purified on a Combiflash unit by Teledyne Isco (4 g silica gel column, 0%→50% ethyl acetate/hexanes) to give the title compound (41 mg, 88%).

5-(3-{(S)-3-Cyano-2-[4-((S)-1-hydroxy-hexyl)-phenyl]-cyclopent-2-enyl}-propyl)-thiophene-2-carboxylic acid methyl ester and 5-(3-{(S)-3-Cyano-2-[4-((R)-1-hydroxy-hexyl)-phenyl]-cyclopent-2-enyl}-propyl)-thiophene-2-carboxylic acid methyl ester (50)

The previously described DDQ procedure was used (US 20060205800). The individual diastereomers could be separated at this stage by HPLC (Phenomenex 50 mm×250 mm silica gel column, 20% ethyl acetate/hexanes, 12 mg/2 mL per injection; retention times 107 and 117 min.)

5-(3-{(S)-3-Cyano-2-[4-((S)-1-hydroxy-hexyl)-phenyl]-cyclopent-2-enyl}-propyl)-thiophene-2-carboxylic acid and 5-(3-{(S)-3-Cyano-2-[4-((R)-1-hydroxy-hexyl)-phenyl]-cyclopent-2-enyl}-propyl)-thiophene-2-carboxylic acid (51)

The above procedure, described for compound 44, was used.

5-(3-{(S)-3-Cyano-2-[4-(1-hydroxy-hexyl)-phenyl]-cyclopent-2-enyl}-propyl)-thiophene-2-carboxylic acid 2-hydroxy-ethyl ester (52, obtained from slower eluting diastereomer of 50)

The previously described procedure was used (U.S. Provisional Application No. 60/986,849, filed Nov. 9, 2007, incorporated by reference herein).

Scheme 10

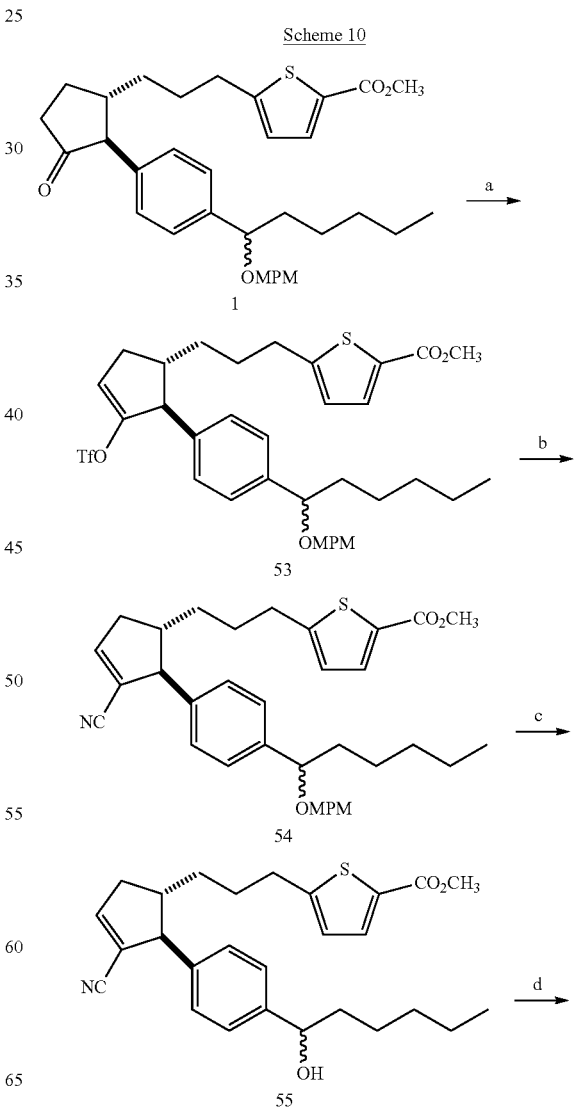

-continued

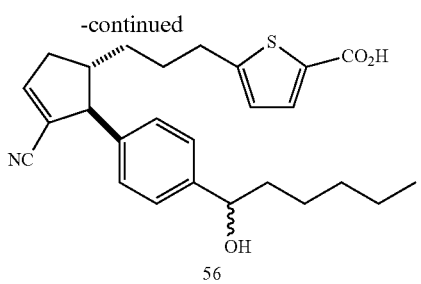

56

Conditions: (a) LiHMDS, THF -78° C.; N-(5-chloro-2-pyridyl)bis(trifluoromethanesulfonamide); (b) NaCN, CuI, Pd(Ph₃P)₄, CH₃CN 90° C.; (c) DDQ, CH₂Cl₂/H₂O; (d) 1M LiOH, THF 60° C.

5-[3-((1S,2S)-3-Cyano-2-{4-[1-(4-methoxy-benzyloxy)-hexyl]-phenyl}-cyclopent-3-enyl)-propyl]-thiophene-2-carboxylic acid methyl ester (53)

A solution of ketone 1 (109 mg, 0.19 mmol) in 0.4 mL THF was added (cannula) to a −78° C. solution of LiHMDS (380 μL, 0.38 mmol, 1 M/THF) in 2 mL THF, rinsing with 0.2 mL THF. After 30 min., a solution of Comin's reagent, N-(5-chloro-2-pyridyl)bis(trifluoromethanesulfonamide), (112 mg, 0.29 mmol) in 0.7 mL THF was added by cannula, rinsing with 0.3 mL THF. The reaction was stirred further 30 min. and then was quenched by addition of 2 mL saturated NH₄Cl solution. The mixture was extracted with ethyl acetate (3×15 mL) and the combined solution was dried (Na₂SO₄), filtered and evaporated. The residue was purified using an Teledyne Isco Combiflash unit (12 g silica gel column, 0%→40% ethyl acetate/hexanes) followed by HPLC (Phenomenex 50 mm×250 mm silica gel column, 10%→15% ethyl acetate/hexanes) which gave the title compound (69 mg, 51%).

5-(3-{(1S,2S)-3-Cyano-2-[4-(1-hydroxy-hexyl)-phenyl]-cyclopent-3-enyl}-propyl)-thiophene-2-carboxylic acid (56)

The remainder of the synthesis was done as shown in scheme 10 and as described above for conversion of 48→51.

Scheme 11

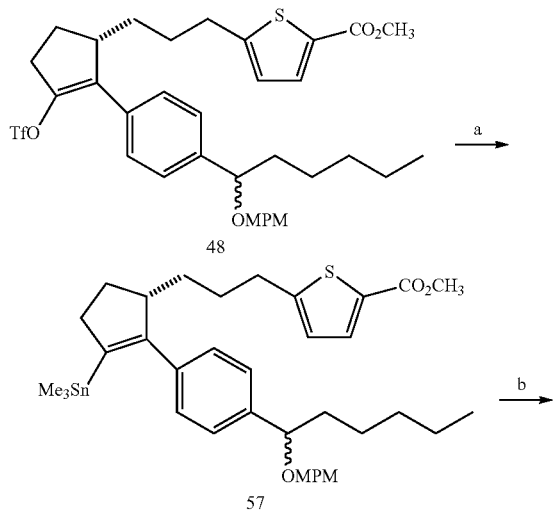

-continued

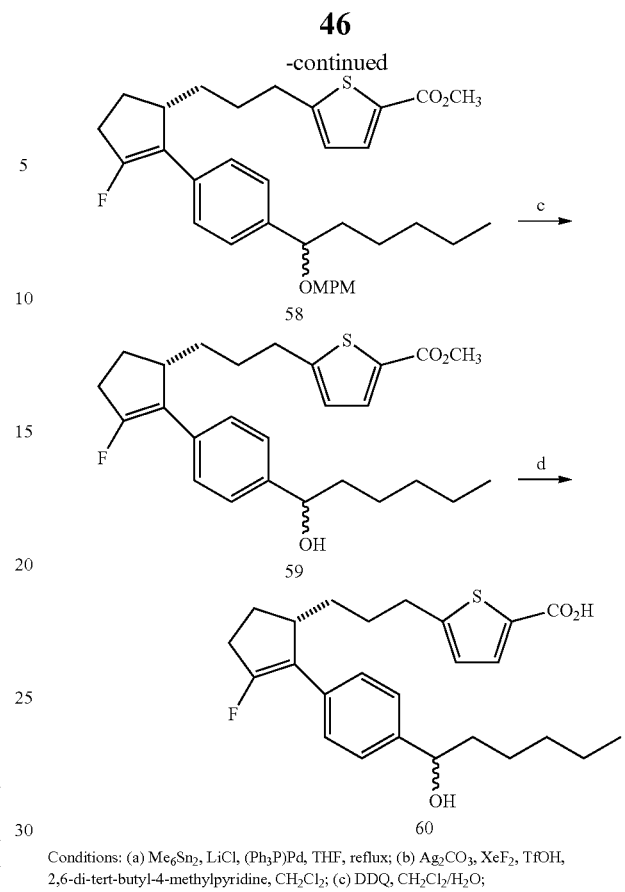

Conditions: (a) Me₆Sn₂, LiCl, (Ph₃P)Pd, THF, reflux; (b) Ag₂CO₃, XeF₂, TfOH, 2,6-di-tert-butyl-4-methylpyridine, CH₂Cl₂; (c) DDQ, CH₂Cl₂/H₂O; (d) 1M LiOH, THF 60° C.

5-[3-((S)-2-{4-[1-(4-Methoxy-benzyloxy)-hexyl]-phenyl}-3-trimethylstannanyl-cyclopent-2-enyl)-propyl]-thiophene-2-carboxylic acid methyl ester (57)

Me₆Sn₂ (120 μL, 0.58 mmol) was added to a mixture of triflate 48 (264 mg, 0.38 mmol), LiCl (196 mg, 4.62 mmol) and (Ph₃P)₄Pd (76 mg, 0.066 mmol) in 15 mL THF. The solution was deoxygenated by bubbling N₂ and then was heated at 76° C. overnight. There was still starting material present (TLC), so more Me₆Sn₃ (250 μL, 1.21 mmol) was added and the mixture was heated at 85° C. overnight. The reaction was then quenched by addition of saturated NaHCO₃ solution (10 mL). The resulting mixture was diluted with 40 mL saturated NaHCO₃ solution and was extracted with ethyl acetate (3×40 mL). The combined solution was washed with 30 mL brine and then was dried (Na₂SO₄), filtered and evaporated.

5-[3-((S)-3-Fluoro-2-{4-[1-(4-methoxy-benzyloxy)-hexyl]-phenyl}-cyclopent-2-enyl)-propyl]-thiophene-2-carboxylic acid methyl ester (58)

An analogous procedure to that described in Marcus A. Tius and Joel K. Kawakami *Tetrahedron* 1995, 51,3997 was used. A solution of triflic acid (37 μL, 0.42 mmol) in 0.37 mL CH₂Cl₂ was added to a mixture of Ag₂CO₃ (83 mg, 0.30 mmol) in 2.8 mL CH₂Cl₂ and the flask was covered in aluminum foil. After 30 min., a solution of 57 (ca. 0.38 mmol, directly from above) and 2,6-di-tert-butyl-4-methylpyridine (49 mg, 0.24 mmol) in 2.8 mL CH₂Cl₂ was added dropwise by cannula, rinsing with 1 mL CH₂Cl₂. At this time, a solution of XeF₂ (82 mg, 0.48 mmol) in 5.5 mL CH₂Cl₂ was added by cannula. The reaction was stirred for 1 h and then was quenched by addition of 10 mL saturated NaHCO₃ solution. The resulting mixture was extracted with CH₂Cl₂ (3×30 mL) and the combined solution was dried (Na₂SO₄), filtered and evaporated. The residue was purified by flash chromatography on a Teledyne Isco Combiflash unit (40 g silica gel column, 0%→100% ethyl acetate/hexanes) followed by HPLC (Phenomenex 50 mm×250 mm silica gel column, 5% ethyl acetate/hexanes) to give the title compound (12 mg, 5%).

5-(3-{(S)-3-Fluoro-2-[4-(1-hydroxy-hexyl)-phenyl]-cyclopent-2-enyl}-propyl)-thiophene-2-carboxylic acid (60)

The conversion of 58→60 was accomplished as shown in scheme 11 using previously described procedures (US 20060205800).

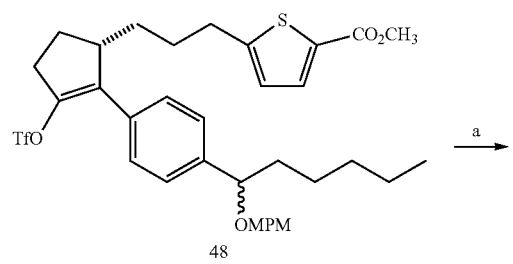
48

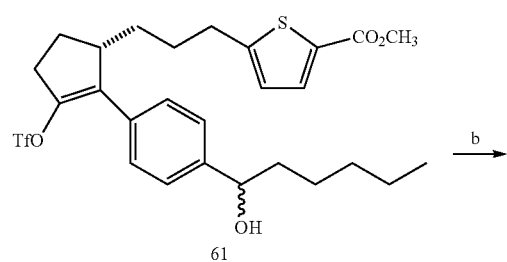
61

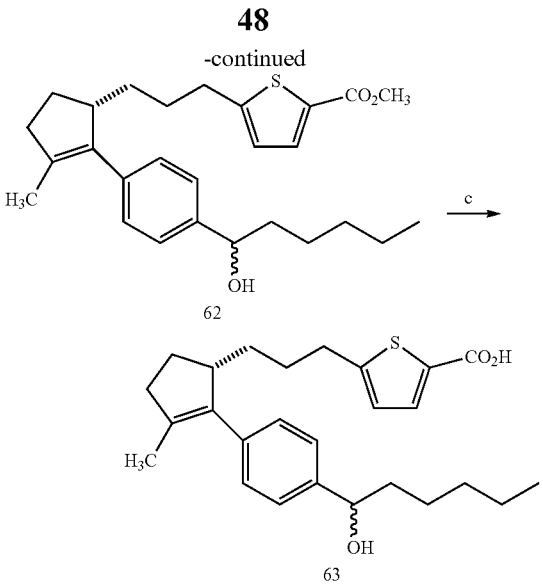
62

63

Conditions: (a) DDQ, CH₂Cl₂/H₂O; (b) MeLi, CuI, THF; (c) (d) 1M LiOH, THF 60° C.

5-(3-{(S)-2-[4-(1-Hydroxy-hexyl)-phenyl]-3-trifluoromethanesulfonyloxy-cyclopent-2-enyl}-propyl)-thiophene-2-carboxylic acid methyl ester (61)

The previously described DDQ procedure was used (US 20060205800).

5-(3-{(S)-2-[4-(1-Hydroxy-hexyl)-phenyl]-3-methyl-cyclopent-2-enyl}-propyl)-thiophene-2-carboxylic acid methyl ester (62)

Methyllithium (300 μL, 0.48 mmol, 1.6 M/ether) was added to an ice cold mixture of CuI (73 mg, 0.38 mmol) in 0.7 it) mL THF. After 30 min., a solution of trflate 61 (53 mg, 0.091 mmol) in 0.3 mL THF was added by cannula, rinsing with 0.3 mL THF. The reaction was stirred at 15° C. overnight and then was allowed to warm to room temperature and further stirred overnight. At this time, the volatiles were evaporated and the residue purified on a Teledyne Isco Combiflash unit (4 g silica gel column, 0%→40% ethyl acetate/hexanes) to give the title compound (7 mg, 16%).

5-(3-{(S)-2-[4-(1-Hydroxy-hexyl)-phenyl]-3-methyl-cyclopent-2-enyl}-propyl)-thiophene-2-carboxylic acid The procedure described for compound 44 was used.

In Vitro Testing

U.S. patent application Ser. No. 11/553,143, filed on Oct. 26, 2006, describes the methods used to obtain the in vitro data in the tables below.

| STRUCTURE | EP2 cAMP EC50 (nM) | EP2 Ki (nM) | EP2 Ca2+ EC50 (nM) | EP4 Ki EC50 (nM) | EP4 Ca2+ EC50 (nM) | OTHER RECEPTORS Ca2+ EC50 (nM) |
|---|---|---|---|---|---|---|
| 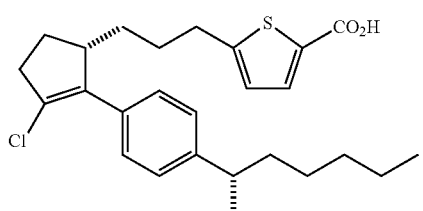 | 0.6 | 16 | 355 | 3679 | >10K | EP3 (1492) NA: EP1, DP, FP, IP, TP |
| 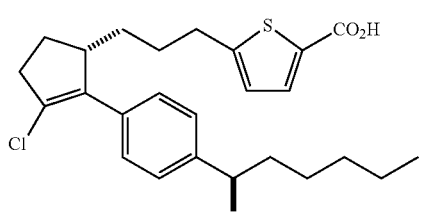 | 0.2 | 5 | 83 | 914 | >10K | NA: EP1, EP3, DP, FP, IP, TP |
| 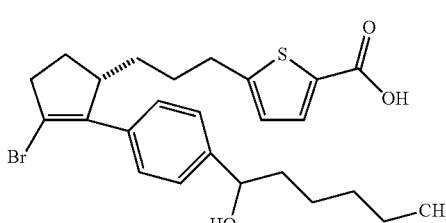 | 0.4 | 1.5 | 403 | 966 | >>10K | EP3 (2341) NA: EP1, DP, FP, IP, TP |
| 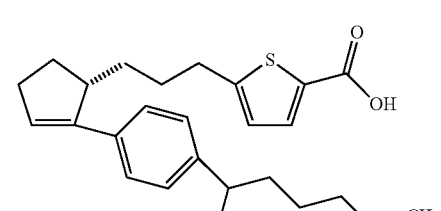 | 0.9 | 5 | 19 | 1182 | >10K | NA: EP1, EP3, DP, FP, IP, TP |
| 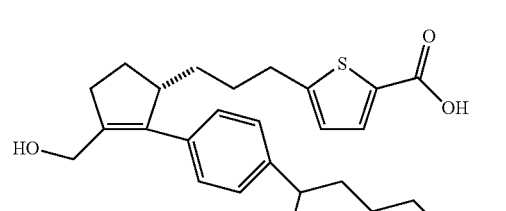 | 48 | 53 | 119 | 1536 | >10K | EP1, EP3 (6976) NA: EP1, DP, FP, IP, TP |
| 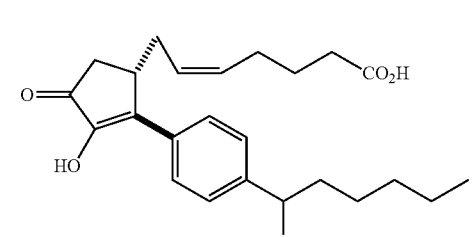 | 54 | 313 | 442 | 785 | >10K | EP3 (9644) NA: EP1, DP, FP, IP, TP |

-continued

| STRUCTURE | EP2 cAMP EC50 (nM) | EP2 Ki (nM) | EP2 Ca2+ EC50 (nM) | EP4 Ki EC50 (nM) | EP4 Ca2+ EC50 (nM) | OTHER RECEPTORS Ca2+ EC50 (nM) |
|---|---|---|---|---|---|---|
| [structure with Br, thiophene-CO2H, OH, CH3] | 0.7 | 5 | 847 | 522 | >>10K | EP3 (3217) NA: EP1, DP, FP, IP, TP |
| [structure with NC, thiophene-CO2H, OH] High T$_R$ | 0.45 | 5 | 74 | >>10K | 2803 | EP3 (3542) NA: EP1, DP, FP, IP, TP |
| [structure with NC, thiophene-CO2H, OH] Low T$_R$ | 0.4 | 3 | 65 | 16041 | 3351 | EP3 (202) NA: EP1, DP, FP, IP, TP |
| [structure with thiophene-CO2H, OH] | 1 | 18 | 27 | | | active: EP3 (3089), DP (7739) NA: EP1, FP, IP, TP |
| [structure with thiophene-CO2H, OH] | 0.8 | 10 | 36 | 16,254 | | active: EP3 (5886), DP (9919) NA: EP1, FP, IP, TP |
| [structure with methyl, thiophene-CO2H, OH] | 4 | 16 | 193 | >10K | 955 | EP3 (7342) NA: EP1, DP, FP, IP, TP |

-continued

| STRUCTURE | EP2 | | | EP4 | | OTHER RECEPTORS Ca2+ EC50 (nM) |
|---|---|---|---|---|---|---|
| | cAMP EC50 (nM) | Ki (nM) | Ca2+ EC50 (nM) | Ki EC50 (nM) | Ca2+ EC50 (nM) | |
| [structure: cyclopentene with F substituent, phenyl with CH(OH)-pentyl chain, propyl-thiophene-CO2H] | 0.2 | 2.4 | 27 | >>10K | 2957 | EP3 (1817) NA: EP1, DP, FP, IP, TP |
| [structure: cyclopentene with NC substituent, phenyl with CH(OH)-pentyl chain, propyl-thiophene-CO2H] | 154 | | 1374 | | 175 | EP3 (8558) NA: EP1, DP, FP, IP, TP |

In Vivo Testing

U.S. Pat. No. 7,091,231 describes the methods used for these in vivo tests.

| | | Conc. (g/100 mL) | Max. ΔIOP (%) | Max. hyperemia | Max. ΔIOP (%) | Max. hyperemia |
|---|---|---|---|---|---|---|
| 1 | [structure: cyclopentene with Cl substituent, phenyl with CH(OH)-pentyl chain, propyl-thiophene-CO2H] (mixture of diastereomers) | 0.01% | 39 | 1.7 | 62 (0.1% dose) | |
| 2 | [structure: cyclopentene with Cl substituent, phenyl with CH(OH)-pentyl chain, propyl-thiophene-CO2iPr] (mixture of diastereomers) | 0.1% | 21 | 1.7 | 26 | |

-continued

| | | Conc. (g/100 mL) | Max. ΔIOP (%) | Max. hyperemia | Max. ΔIOP (%) | Max. hyperemia |
|---|---|---|---|---|---|---|
| 3 | (structure) slower eluting diastereomer | 0.003 | 35 | 1.3 | 46 | |
| 4 | (structure) faster eluting diastereomer | 0.003 | 35 | 1.4 | 39 | |
| 5 | (structure) | 0.01 | 41 | 1.9 | 53 | |
| 6 | (structure) | 0.01 | 32 | 2.0 | 31 | |
| 7 | (structure) | 0.01 | 37 | 1.8 | | |

TREATMENT EXAMPLES

The following are hypothetical examples demonstrating how a person may be treated with the compounds disclosed herein.

Treatment Example 1

An aqueous liquid containing 0.1% of H1 is given topically to the eye of a person suffering from elevated intraocular pressure. A few hours after administration, the person's intraocular pressure is reduced. The drop is administered twice a day, and pressure remains low for as long as the treatment is continued.

Treatment Example 2

An aqueous liquid containing 0.1% of H2 is given topically to the eye of a person suffering from elevated intraocular pressure. A few hours after administration, the person's intraocular pressure is reduced. The drop is administered twice a day, and pressure remains low for as long as the treatment is continued.

Treatment Example 3

An aqueous liquid containing 0.1% of H3 is given topically to the eye of a person suffering from elevated intraocular pressure. A few hours after administration, the person's intraocular pressure is reduced. The drop is administered twice a day, and pressure remains low for as long as the treatment is continued.

Treatment Example 4

An aqueous liquid containing 0.1% of H4 is given topically to the eye of a person suffering from elevated intraocular pressure. A few hours after administration, the person's intraocular pressure is reduced. The drop is administered twice a day, and pressure remains low for as long as the treatment is continued.

Treatment Example 5

An aqueous liquid containing 0.1% of H5 is given topically to the eye of a person suffering from elevated intraocular pressure. A few hours after administration, the person's intraocular pressure is reduced. The drop is administered twice a day, and pressure remains low for as long as the treatment is continued.

Treatment Example 6

An aqueous liquid containing 0.1% of H6 is given topically to the eye of a person suffering from elevated intraocular pressure. A few hours after administration, the person's intraocular pressure is reduced. The drop is administered twice a day, and pressure remains low for as long as the treatment is continued.

Treatment Example 7

An aqueous liquid containing 0.1% of H7 is given topically to the eye of a person suffering from elevated intraocular pressure. A few hours after administration, the person's intraocular pressure is reduced. The drop is administered twice a day, and pressure remains low for as long as the treatment is continued.

Treatment Example 8

An aqueous liquid containing 0.1% of H8 is given topically to the eye of a person suffering from elevated intraocular pressure. A few hours after administration, the person's intraocular pressure is reduced. The drop is administered twice a day, and pressure remains low for as long as the treatment is continued.

H1

-continued

H2

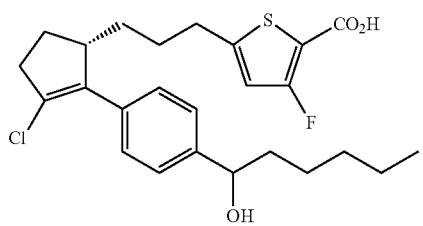

H3

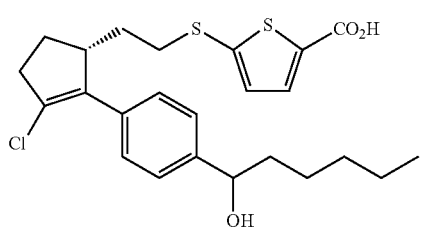

H4

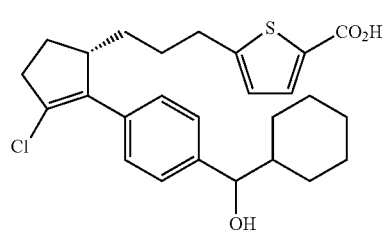

H5

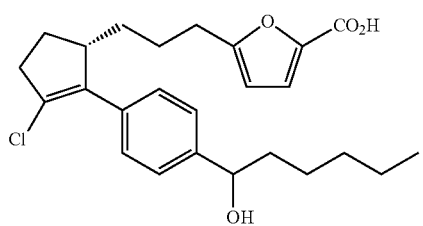 [SMILES: CCCCC[C@H](O)c1ccc(C2=C(Cl)CC[C@@H]2CCCc2ccc(C(=O)O)s2)cc1]

H6

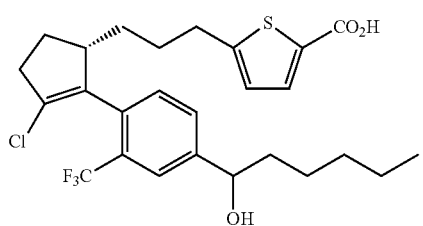

H7

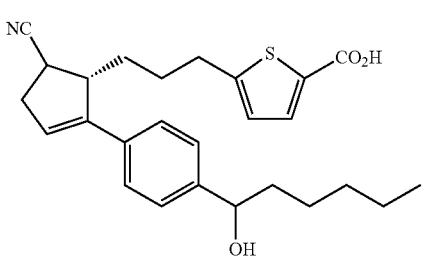

-continued

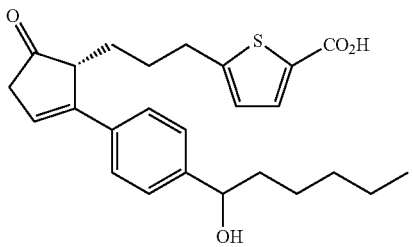

H8

Treatment Example 9

An aqueous liquid containing 0.1% of H9 is given topically to the eye of a person suffering from elevated intraocular pressure. A few hours after administration, the person's intraocular pressure is reduced. The drop is administered twice a day, and pressure remains low for as long as the treatment is continued.

Treatment Example 10

An aqueous liquid containing 0.1% of H10 is given topically to the eye of a person suffering from elevated intraocular pressure. A few hours after administration, the person's intraocular pressure is reduced. The drop is administered twice a day, and pressure remains low for as long as the treatment is continued.

Treatment Example 11

An aqueous liquid containing 0.1% of H11 is given topically to the eye of a person suffering from elevated intraocular pressure. A few hours after administration, the person's intraocular pressure is reduced. The drop is administered twice a day, and pressure remains low for as long as the treatment is continued.

Treatment Example 12

An aqueous liquid containing 0.1% of H12 is given topically to the eye of a person suffering from elevated intraocular pressure. A few hours after administration, the person's intraocular pressure is reduced. The drop is administered twice a day, and pressure remains low for as long as the treatment is continued.

Treatment Example 13

An aqueous liquid containing 0.1% of H13 is given topically to the eye of a person suffering from elevated intraocular pressure. A few hours after administration, the person's intraocular pressure is reduced. The drop is administered twice a day, and pressure remains low for as long as the treatment is continued.

Treatment Example 14

An aqueous liquid containing 0.1% of H14 is given topically to the eye of a person suffering from elevated intraocular pressure. A few hours after administration, the person's intraocular pressure is reduced. The drop is administered twice a day, and pressure remains low for as long as the treatment is continued.

Treatment Example 15

An aqueous liquid containing 0.1% of H15 is given topically to the eye of a person suffering from elevated intraocular pressure. A few hours after administration, the person's intraocular pressure is reduced. The drop is administered twice a day, and pressure remains low for as long as the treatment is continued.

Treatment Example 16

An aqueous liquid containing 0.1% of H16 is given topically to the eye of a person suffering from elevated intraocular pressure. A few hours after administration, the person's intraocular pressure is reduced. The drop is administered twice a day, and pressure remains low for as long as the treatment is continued.

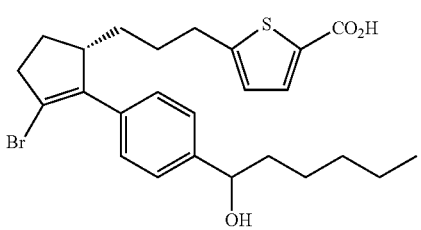

H9

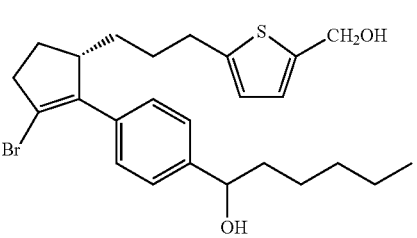

H10

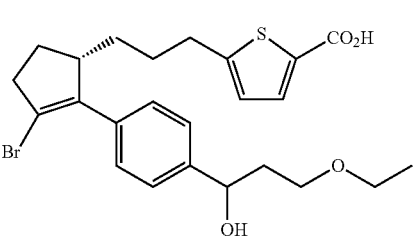

H11

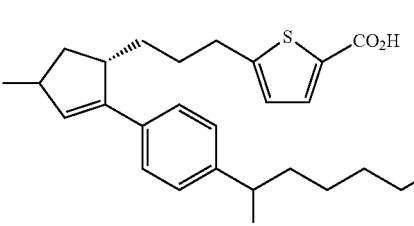

H12

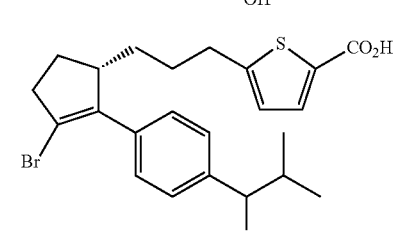

H13

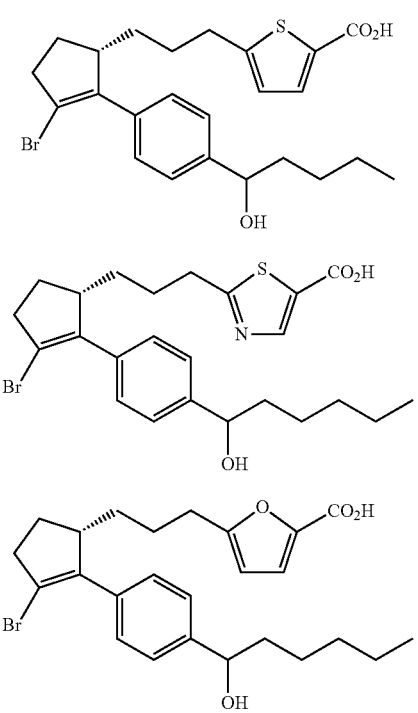

H14

H15

H16

Treatment Example 17

An aqueous liquid containing 0.1% of H17 is given topically to the eye of a person suffering from elevated intraocular pressure. A few hours after administration, the person's intraocular pressure is reduced. The drop is administered twice a day, and pressure remains low for as long as the treatment is continued.

Treatment Example 18

An aqueous liquid containing 0.1% of H18 is given topically to the eye of a person suffering from elevated intraocular pressure. A few hours after administration, the person's intraocular pressure is reduced. The drop is administered twice a day, and pressure remains low for as long as the treatment is continued.

Treatment Example 19

An aqueous liquid containing 0.1% of H19 is given topically to the eye of a person suffering from elevated intraocular pressure. A few hours after administration, the person's intraocular pressure is reduced. The drop is administered twice a day, and pressure remains low for as long as the treatment is continued.

Treatment Example 20

An aqueous liquid containing 0.1% of H20 is given topically to the eye of a person suffering from elevated intraocular pressure. A few hours after administration, the person's intraocular pressure is reduced. The drop is administered twice a day, and pressure remains low for as long as the treatment is continued.

Treatment Example 21

An aqueous liquid containing 0.1% of H21 is given topically to the eye of a person suffering from elevated intraocular pressure. A few hours after administration, the person's intraocular pressure is reduced. The drop is administered twice a day, and pressure remains low for as long as the treatment is continued.

Treatment Example 22

An aqueous liquid containing 0.1% of H22 is given topically to the eye of a person suffering from elevated intraocular pressure. A few hours after administration, the person's intraocular pressure is reduced. The drop is administered twice a day, and pressure remains low for as long as the treatment is continued.

Treatment Example 23

An aqueous liquid containing 0.1% of H23 is given topically to the eye of a person suffering from elevated intraocular pressure. A few hours after administration, the person's intraocular pressure is reduced. The drop is administered twice a day, and pressure remains low for as long as the treatment is continued.

Treatment Example 24

An aqueous liquid containing 0.1% of H24 is given topically to the eye of a person suffering from elevated intraocular pressure. A few hours after administration, the person's intraocular pressure is reduced. The drop is administered twice a day, and pressure remains low for as long as the treatment is continued.

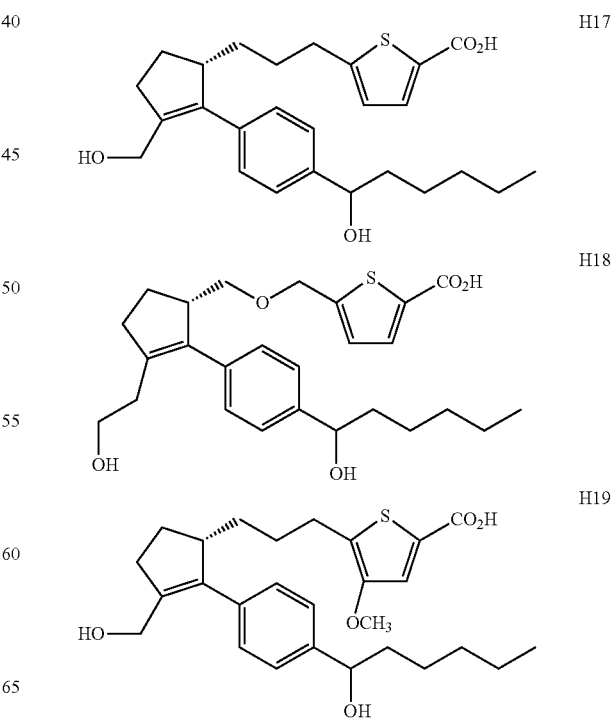

H17

H18

H19

-continued

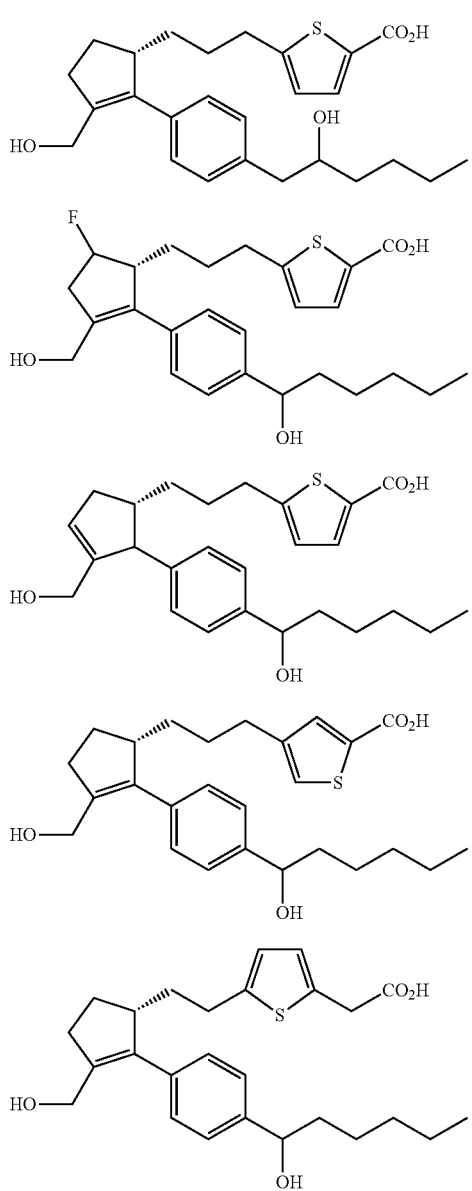

Treatment Example 25

An aqueous liquid containing 0.1% of H25 is given topically to the eye of a person suffering from elevated intraocular pressure. A few hours after administration, the person's intraocular pressure is reduced. The drop is administered twice a day, and pressure remains low for as long as the treatment is continued.

Treatment Example 26

An aqueous liquid containing 0.1% of H26 is given topically to the eye of a person suffering from elevated intraocular pressure. A few hours after administration, the person's intraocular pressure is reduced. The drop is administered twice a day, and pressure remains low for as long as the treatment is continued.

Treatment Example 27

An aqueous liquid containing 0.1% of H27 is given topically to the eye of a person suffering from elevated intraocular pressure. A few hours after administration, the person's intraocular pressure is reduced. The drop is administered twice a day, and pressure remains low for as long as the treatment is continued.

Treatment Example 28

An aqueous liquid containing 0.1% of H28 is given topically to the eye of a person suffering from elevated intraocular pressure. A few hours after administration, the person's intraocular pressure is reduced. The drop is administered twice a day, and pressure remains low for as long as the treatment is continued.

Treatment Example 29

An aqueous liquid containing 0.1% of H29 is given topically to the eye of a person suffering from elevated intraocular pressure. A few hours after administration, the person's intraocular pressure is reduced. The drop is administered twice a day, and pressure remains low for as long as the treatment is continued.

Treatment Example 30

An aqueous liquid containing 0.1% of H30 is given topically to the eye of a person suffering from elevated intraocular pressure. A few hours after administration, the person's intraocular pressure is reduced. The drop is administered twice a day, and pressure remains low for as long as the treatment is continued.

Treatment Example 31

An aqueous liquid containing 0.1% of H31 is given topically to the eye of a person suffering from elevated intraocular pressure. A few hours after administration, the person's intraocular pressure is reduced. The drop is administered twice a day, and pressure remains low for as long as the treatment is continued.

Treatment Example 32

An aqueous liquid containing 0.1% of H32 is given topically to the eye of a person suffering from elevated intraocular pressure. A few hours after administration, the person's intraocular pressure is reduced. The drop is administered twice a day, and pressure remains low for as long as the treatment is continued.

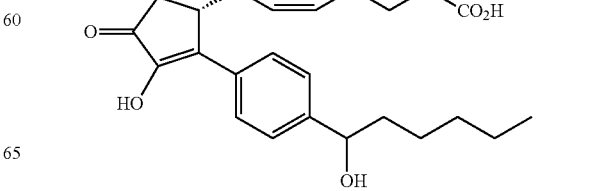

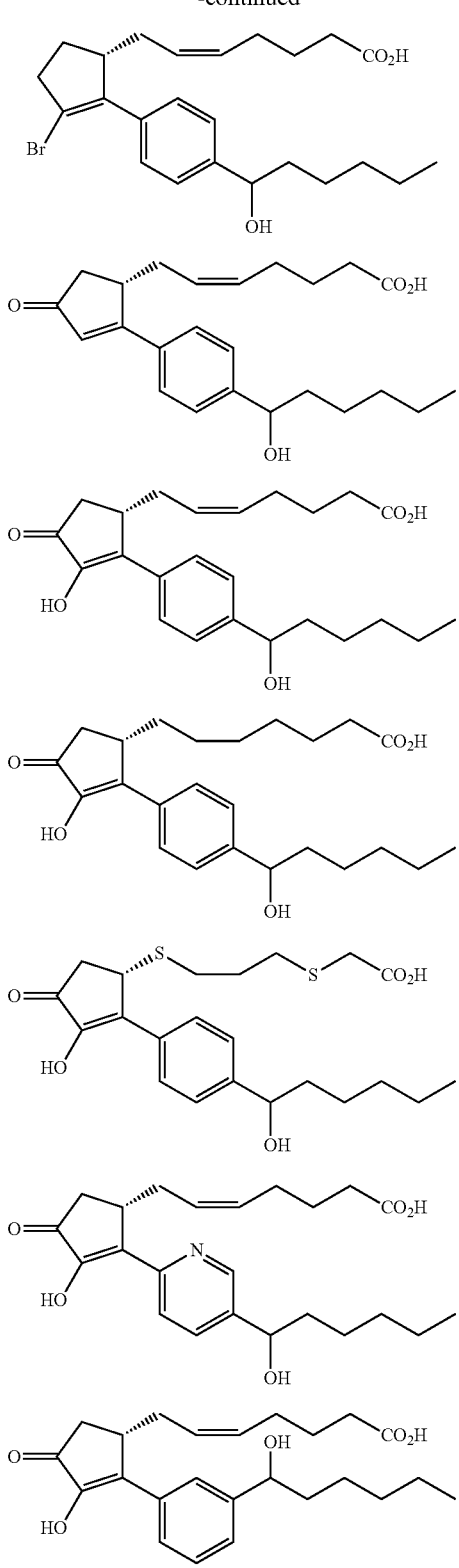

Treatment Example 33

An aqueous liquid containing 0.1% of H33 is given topically to the eye of a person suffering from elevated intraocular pressure. A few hours after administration, the person's intraocular pressure is reduced. The drop is administered twice a day, and pressure remains low for as long as the treatment is continued.

Treatment Example 34

An aqueous liquid containing 0.1% of H34 is given topically to the eye of a person suffering from elevated intraocular pressure. A few hours after administration, the person's intraocular pressure is reduced. The drop is administered twice a day, and pressure remains low for as long as the treatment is continued.

Treatment Example 35

An aqueous liquid containing 0.1% of H35 is given topically to the eye of a person suffering from elevated intraocular pressure. A few hours after administration, the person's intraocular pressure is reduced. The drop is administered twice a day, and pressure remains low for as long as the treatment is continued.

Treatment Example 36

An aqueous liquid containing 0.1% of H36 is given topically to the eye of a person suffering from elevated intraocular pressure. A few hours after administration, the person's intraocular pressure is reduced. The drop is administered twice a day, and pressure remains low for as long as the treatment is continued.

Treatment Example 37

An aqueous liquid containing 0.1% of H37 is given topically to the eye of a person suffering from elevated intraocular pressure. A few hours after administration, the person's intraocular pressure is reduced. The drop is administered twice a day, and pressure remains low for as long as the treatment is continued.

Treatment Example 38

An aqueous liquid containing 0.1% of H38 is given topically to the eye of a person suffering from elevated intraocular pressure. A few hours after administration, the person's intraocular pressure is reduced. The drop is administered twice a day, and pressure remains low for as long as the treatment is continued.

Treatment Example 39

An aqueous liquid containing 0.1% of H39 is given topically to the eye of a person suffering from elevated intraocular pressure. A few hours after administration, the person's intraocular pressure is reduced. The drop is administered twice a day, and pressure remains low for as long as the treatment is continued.

Treatment Example 40

An aqueous liquid containing 0.1% of H40 is given topically to the eye of a person suffering from elevated intraocular pressure. A few hours after administration, the person's intraocular pressure is reduced. The drop is administered twice a day, and pressure remains low for as long as the treatment is continued.

H33 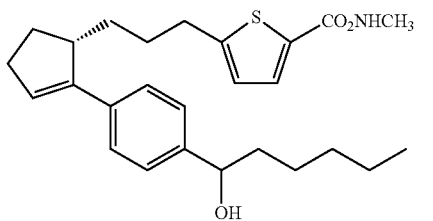

H34 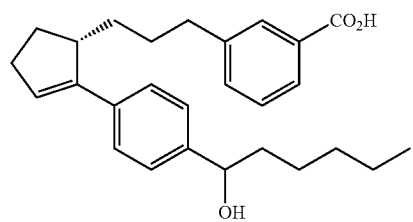

H35 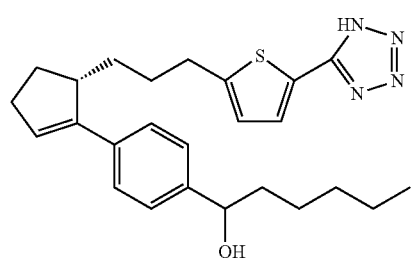

H36 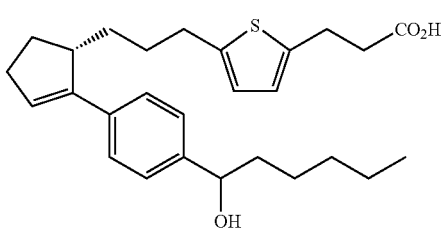

H37 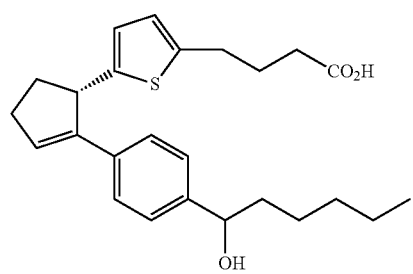

H38 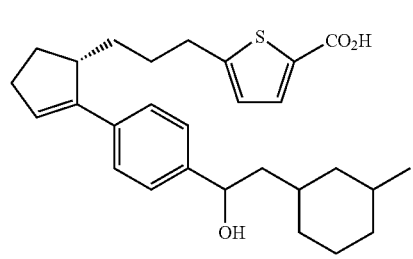

H39 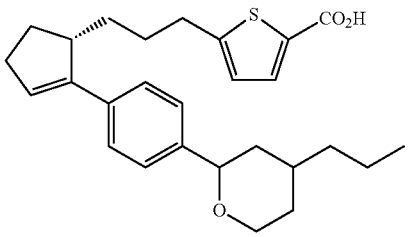

H40 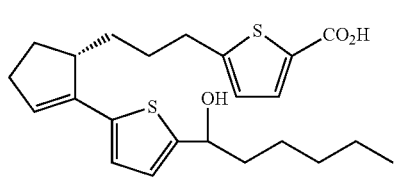

Treatment Example 41

An aqueous liquid containing 0.1% of H41 is given topically to the eye of a person suffering from elevated intraocular pressure. A few hours after administration, the person's intraocular pressure is reduced. The drop is administered twice a day, and pressure remains low for as long as the treatment is continued.

Treatment Example 42

An aqueous liquid containing 0.1% of H42 is given topically to the eye of a person suffering from elevated intraocular pressure. A few hours after administration, the person's intraocular pressure is reduced. The drop is administered twice a day, and pressure remains low for as long as the treatment is continued.

Treatment Example 43

An aqueous liquid containing 0.1% of H43 is given topically to the eye of a person suffering from elevated intraocular pressure. A few hours after administration, the person's intraocular pressure is reduced. The drop is administered twice a day, and pressure remains low for as long as the treatment is continued.

Treatment Example 44

An aqueous liquid containing 0.1% of H44 is given topically to the eye of a person suffering from elevated intraocular pressure. A few hours after administration, the person's intraocular pressure is reduced. The drop is administered twice a day, and pressure remains low for as long as the treatment is continued.

Treatment Example 45

An aqueous liquid containing 0.1% of H45 is given topically to the eye of a person suffering from elevated intraocular pressure. A few hours after administration, the person's intraocular pressure is reduced. The drop is administered twice a day, and pressure remains low for as long as the treatment is continued.

Treatment Example 46

An aqueous liquid containing 0.1% of H46 is given topically to the eye of a person suffering from elevated intraocular pressure. A few hours after administration, the person's intraocular pressure is reduced. The drop is administered twice a day, and pressure remains low for as long as the treatment is continued.

Treatment Example 47

An aqueous liquid containing 0.1% of H47 is given topically to the eye of a person suffering from elevated intraocular pressure. A few hours after administration, the person's intraocular pressure is reduced. The drop is administered twice a day, and pressure remains low for as long as the treatment is continued.

Treatment Example 48

An aqueous liquid containing 0.1% of H48 is given topically to the eye of a person suffering from elevated intraocular pressure. A few hours after administration, the person's intraocular pressure is reduced. The drop is administered twice a day, and pressure remains low for as long as the treatment is continued.

Treatment Example 49

An aqueous liquid containing 0.1% of H49 is given topically to the eye of a person suffering from elevated intraocular pressure. A few hours after administration, the person's intraocular pressure is reduced. The drop is administered twice a day, and pressure remains low for as long as the treatment is continued.

Treatment Example 50

An aqueous liquid containing 0.1% of H50 is given topically to the eye of a person suffering from elevated intraocular pressure. A few hours after administration, the person's intraocular pressure is reduced. The drop is administered twice a day, and pressure remains low for as long as the treatment is continued.

Treatment Example 51

An aqueous liquid containing 0.1% of H51 is given topically to the eye of a person suffering from elevated intraocular pressure. A few hours after administration, the person's intraocular pressure is reduced. The drop is administered twice a day, and pressure remains low for as long as the treatment is continued.

Treatment Example 52

An aqueous liquid containing 0.1% of H52 is given topically to the eye of a person suffering from elevated intraocular pressure. A few hours after administration, the person's intraocular pressure is reduced. The drop is administered twice a day, and pressure remains low for as long as the treatment is continued.

Treatment Example 53

An aqueous liquid containing 0.1% of H53 is given topically to the eye of a person suffering from elevated intraocular pressure. A few hours after administration, the person's intraocular pressure is reduced. The drop is administered twice a day, and pressure remains low for as long as the treatment is continued.

Treatment Example 54

An aqueous liquid containing 0.1% of H54 is given topically to the eye of a person suffering from elevated intraocular pressure. A few hours after administration, the person's intraocular pressure is reduced. The drop is administered twice a day, and pressure remains low for as long as the treatment is continued.

Treatment Example 55

An aqueous liquid containing 0.1% of H55 is given topically to the eye of a person suffering from elevated intraocular pressure. A few hours after administration, the person's intraocular pressure is reduced. The drop is administered twice a day, and pressure remains low for as long as the treatment is continued.

Treatment Example 56

An aqueous liquid containing 0.1% of H56 is given topically to the eye of a person suffering from elevated intraocular pressure. A few hours after administration, the person's intraocular pressure is reduced. The drop is administered twice a day, and pressure remains low for as long as the treatment is continued.

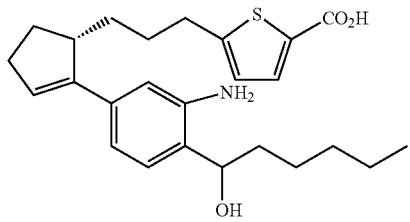 [SMILES: CCCCC[C@H](O)c1ccc(C2=CCC[C@@H]2CCCc2ccc(C(=O)O)s2)cc1]

H49

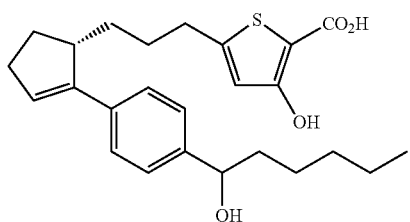 [SMILES: CCCCC[C@H](O)c1ccc(C2=CCC[C@@H]2CCCc2ccc(C(=O)O)s2)cc1]

H50

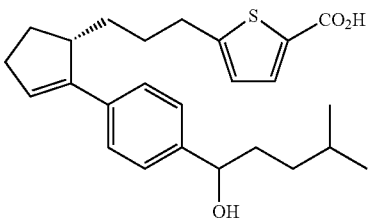

H51

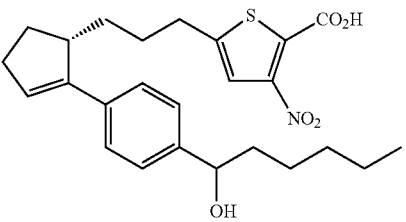

H52

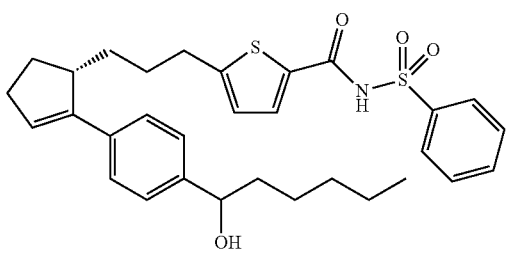

H53

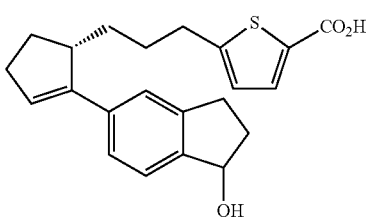

H54

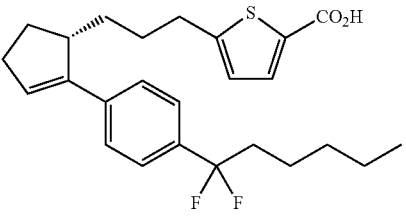

H55

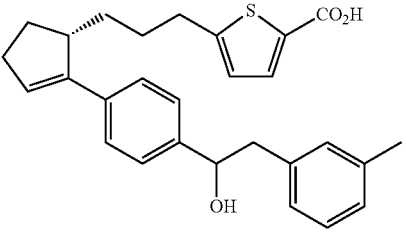

H56

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

What is claimed is:
1. A compound of Formula I or II:
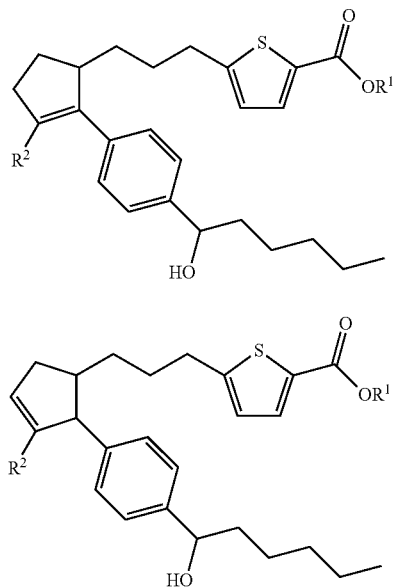
or a pharmaceutically acceptable salt thereof, wherein:
R¹ is hydrogen, C₁ to C₃ alkyl, or CH₂CH₂OH; and
R² is hydrogen, halogen, CH₂OH, CH₃, or CN.
2. The compound according to claim 1, wherein the compound is a compound of the formula:
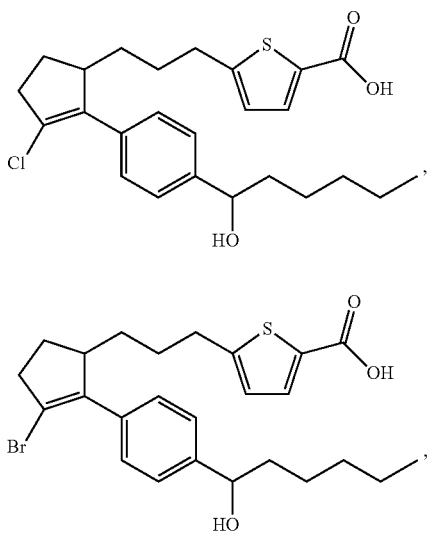
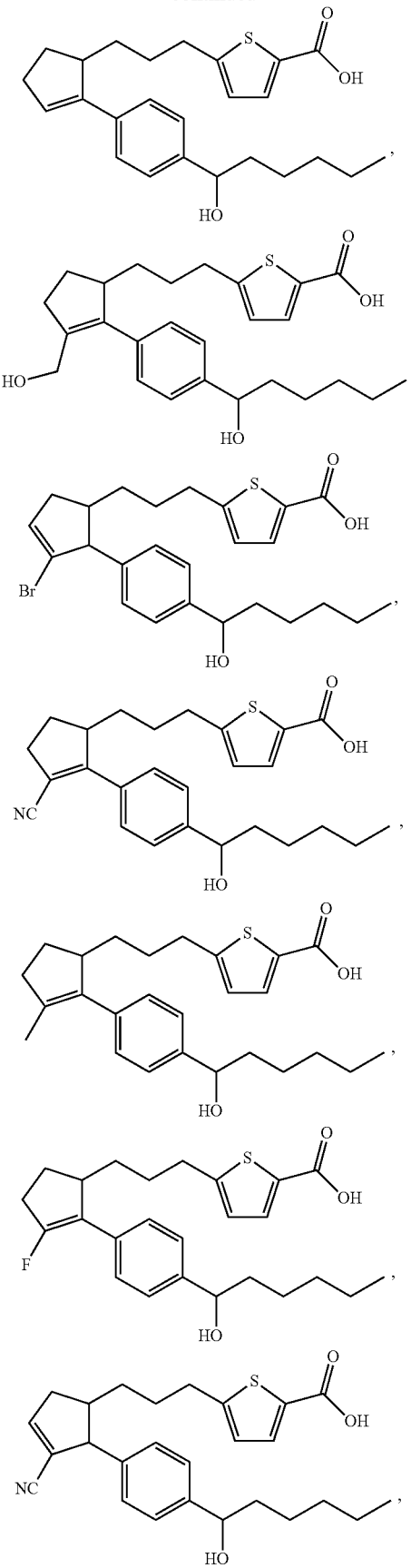

-continued

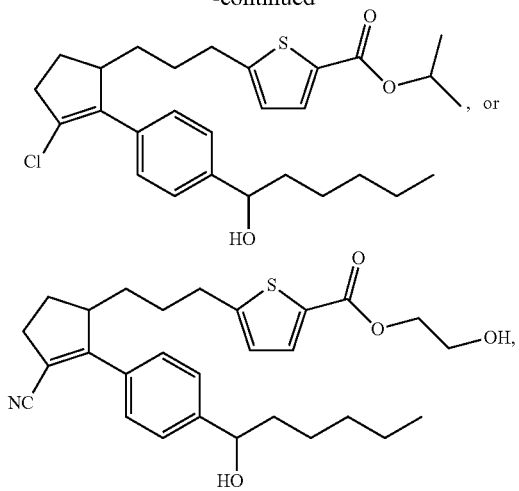

, or or a pharmaceutically acceptable salt thereof.

3. A composition comprising a compound according to claim 1, wherein said composition is a liquid which is ophthalmically acceptable.

4. A method for treating glaucoma or ocular hypertension comprising administering to a subject in need thereof a therapeutically effective amount of a compound according to claim 1.

5. A compound of the formula:

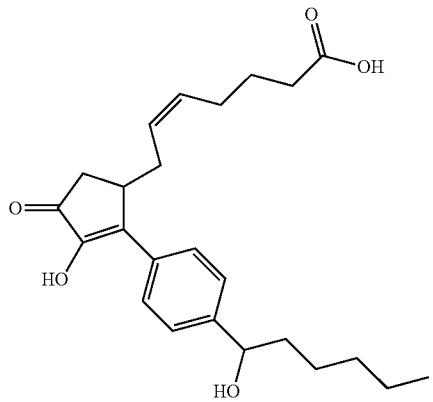 [SMILES: CCCCCC(O)c1ccc(C2=C(O)C(=O)CC2C/C=C\CCCC(=O)O)cc1]

or a pharmaceutically acceptable salt thereof.

6. A composition comprising a compound according to claim 5, wherein said composition is a liquid which is ophthalmically acceptable.

7. A method for treating glaucoma or ocular hypertension comprising administering to a subject in need thereof a therapeutically effective amount of a compound according to claim 5.

* * * * *